US010172976B2

(12) United States Patent
Lancaster et al.

(10) Patent No.: US 10,172,976 B2
(45) Date of Patent: Jan. 8, 2019

(54) MUSCLE CELL PATCHES AND USES THEREFOR

(71) Applicants: ARIZONA BOARD OF REGENTS ON BEHALF OF THE UNIVERSITY OF ARIZONA, Tucson, AZ (US); The United States of America As Represented By The Department Of Veterans Affairs, Washington, DC (US)

(72) Inventors: Jordan J. Lancaster, Tucson, AZ (US); Steven Goldman, Tucson, AZ (US)

(73) Assignees: ARIZONA BOARD OF REGENTS ON BEHALF OF THE UNIVERSITY OF ARIZONA, Tucson, AZ (US); THE UNITED STATES OF AMERICA AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 0 days.

(21) Appl. No.: 15/028,606

(22) PCT Filed: Oct. 8, 2014

(86) PCT No.: PCT/US2014/059688
§ 371 (c)(1),
(2) Date: Apr. 11, 2016

(87) PCT Pub. No.: WO2015/054383
PCT Pub. Date: Apr. 16, 2015

(65) Prior Publication Data
US 2016/0250384 A1 Sep. 1, 2016

Related U.S. Application Data

(60) Provisional application No. 61/888,882, filed on Oct. 9, 2013.

(51) Int. Cl.
*A61L 27/38* (2006.01)
*C12N 5/00* (2006.01)
(Continued)

(52) U.S. Cl.
CPC .......... *A61L 27/3826* (2013.01); *A61K 35/34* (2013.01); *A61K 38/18* (2013.01);
(Continued)

(58) Field of Classification Search
None
See application file for complete search history.

(56) References Cited

U.S. PATENT DOCUMENTS

| 2008/0145344 A1 | 6/2008 | Deshpande et al. |
| 2009/0169521 A1 | 7/2009 | Levenberg et al. |
| 2012/0128637 A1 | 5/2012 | Lancaster et al. |

FOREIGN PATENT DOCUMENTS

| JP | 6-503810 | 4/1994 |
| JP | 2008-518998 | 6/2008 |

(Continued)

OTHER PUBLICATIONS

De Coppi, Paolo; et al; "Myoblast—Acellular Skeletal Muscle Matrix Constructs Guarantee a Long-Term Repair of Experimental Full-Thickness Abdominal Wall Defects" Tissue Engineering, 12, 1929-1936, 2006. (Year: 2006).*

(Continued)

*Primary Examiner* — David W Berke-Schlessel
(74) *Attorney, Agent, or Firm* — Casimir Jones, S.C.; Robert A. Goetz

(57) ABSTRACT

Disclosed herein are contractile cell constructs comprising contractile cells, or progenitors thereof, adhered to a surface of a three dimensional fibroblast containing scaffold (3DFCS) and methods for using them to treat disease. In one aspect, the present invention provides methods for preparing (Continued)

a contractile construct, comprising (a) seeding immature contractile cells onto the surface of a three dimensional fibroblast containing scaffold (3DFCS) to produce a contractile construct; and (b) culturing the contractile construct under conditions to promote differentiation of the immature contractile cells into mature contractile cells, wherein the mature contractile cells form striations. In a further aspect, the invention provides methods for treating a disorder characterized by a lack of functioning contractile cells, comprising contacting a patient with a contractile cell-based disorder with an amount effective to treat the disorder with the construct of any embodiment or combination of embodiments of the invention.

16 Claims, 8 Drawing Sheets

(51) Int. Cl.
      *A61L 27/36*      (2006.01)
      *C12N 5/077*     (2010.01)
      *A61L 27/58*      (2006.01)
      *A61L 27/54*      (2006.01)
      *A61K 35/34*     (2015.01)
      *A61K 38/18*     (2006.01)
      *A61K 38/22*     (2006.01)
(52) U.S. Cl.
      CPC ........ *A61K 38/2292* (2013.01); *A61L 27/367* (2013.01); *A61L 27/3873* (2013.01); *A61L 27/54* (2013.01); *A61L 27/58* (2013.01); *C12N 5/0062* (2013.01); *C12N 5/0657* (2013.01); *A61L 2300/412* (2013.01); *A61L 2300/64* (2013.01); *A61L 2430/20* (2013.01); *C12N 2506/1315* (2013.01); *C12N 2513/00* (2013.01); *C12N 2527/00* (2013.01)

(56) References Cited

FOREIGN PATENT DOCUMENTS

| WO | 92/04033 | 3/1992 |
|---|---|---|
| WO | 2006/048329 | 5/2006 |
| WO | 2012/117855 | 9/2012 |
| WO | 2013/056019 A1 | 4/2013 |

OTHER PUBLICATIONS

International Search Report for PCT/US2014/59688, dated Dec. 23, 2014.
Jung, et al: "hiPSC Modeling of Inherited Cardiomyopathies", Current Treatment Options in Cardiovascular Medicine, vol. 16, No. 7, May 17, 2014.
Kawaguchi, et al: "3D-Culture System for Heart Regeneration and Cardiac Medicine". Biomed Research International, vol. 2013, Jan. 1, 2013 (Jan. 1, 2013), pp. 1-6.
Knollmann: "Induced Pluripotent Stem Cell-Derived Cardiomyocytes: Boutique Science or Valuable Arrhythmia Model?", Circulation Research., vol. 112, No. 6. Mar. 15, 2013 (Mar. 15, 2013), pp. 969-976.
Kreutziger, et al: "Engineered Human Cardiac Tissue". Pediatric Cardiology, vol. 32, No. 3. Feb. 4, 2011 (Feb. 4, 2011), pp. 334-341.
Lancaster, et al: "Construction of a Spontaneously Contracting Biologically Active Cardiomyocyte Scaffold," Journal of Cardial Failure, vol. 15, No. 6, Aug. 1, 2009 (Aug. 1, 2009), pp. S44-S45.
Lancaster, et al: "An electrically coupled tissue-engineered cardiomyocyte scaffold improves cardiac function in rats with chronic heart failure", Journal of Heart and Lung Transplantation, vol. 33, No. 4, Dec. 17, 2013 (Dec. 17, 2013), pp. 438-445.
Shiba, et al: "Cardiac Applications for Human Pluripotent Stem Cells", Current Pharmaceutical Design, vol. 15, No. 24, Aug. 1, 2009 (Aug. 1, 2009). pp. 2791-2806.
Ye, et al: "Patching the Heart: Cardiac Repair From Within and Outside", Circulation Research, vol. 113. No. 7. Sep. 13, 2013 (Sep. 13, 2013), pp. 922-932.
Zakharova, et al: "Transplantation of cardiac progenitor cell sheet onto infarcted heart promotes cardiogenesis and improves function", Cardiovascular Research, vol. 87, No. 1, Jan. 29, 2010 (Jan. 29, 2010), pp. 40-49.
Supplementary European Search Report for EP 14852537, dated Mar. 6, 2017.
JP Office Action, JP Patent Application No. 2016-547972, dated Jun. 19, 2018, 11 pages.

\* cited by examiner

FIGURE 1a – 1c
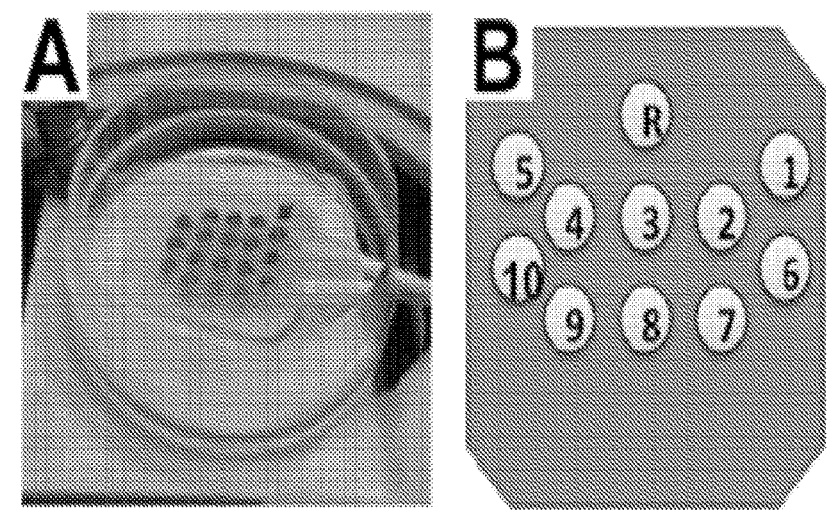
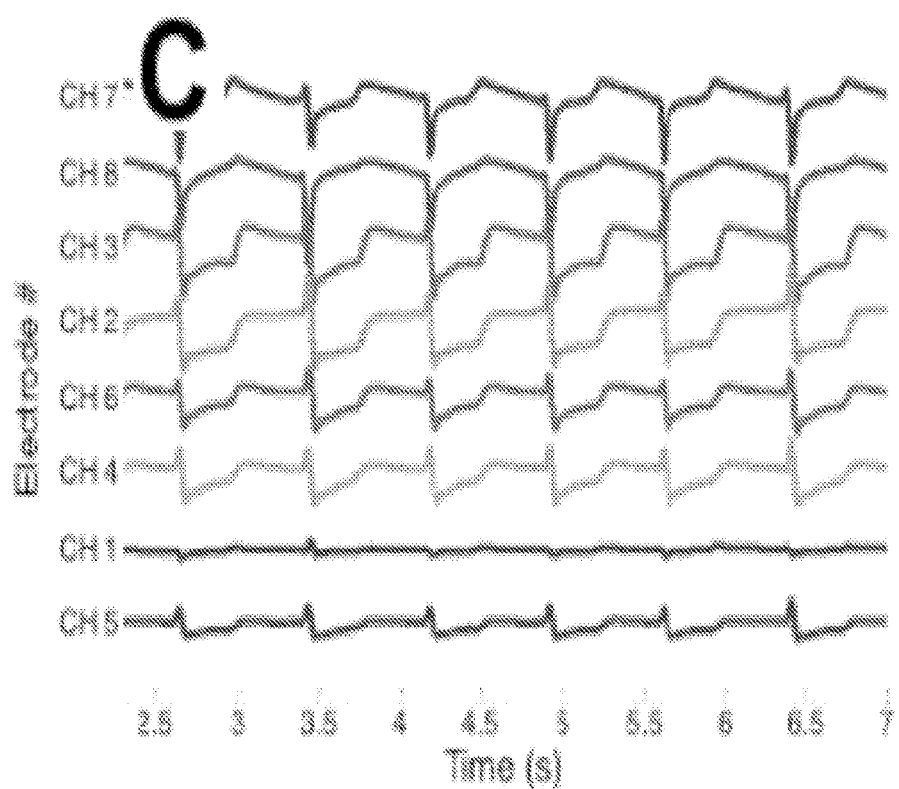

MUSCLE CELL PATCHES AND USES THEREFOR

CROSS REFERENCE

This application is a U.S. national phase of International Application No. PCT/US2014/059688, filed on Oct. 8, 2014, which claims priority to U.S. Provisional Application No. 61/888,882, filed Oct. 9, 2013, both of which are incorporated by reference herein in their entirety.

STATEMENT OF GOVERNMENT RIGHTS

This invention was made with government support under grant no. 1-101-BX001406-01A1 awarded by the VA. The government has certain rights in the invention

BACKGROUND

New treatments are needed for patients with chronic heart failure (CHF), the No. 1 hospital discharge diagnosis in patients over the age of 65 years of age in this country, as well as related ischemic and non-ischemic cardiac disorders. The prevalence of heart failure is over 5 million; the incidence is 550,000 patients per year. Heart failure results in more deaths than cancer, accidents, and strokes combined, costing more than $23 billion annually. Once a patient becomes symptomatic with NY Class III or IV heart failure, their mortality approaches 50% in two years without a heart transplant. The newest approach to treat CHF is to inject stem cells and/or progenitor cells directly into the heart using a number of different cell types. However, the results from recent clinical trials using such injection strategies are generally disappointing.

SUMMARY OF THE INVENTION

In one aspect, the present invention provides methods for preparing a contractile construct, comprising
(a) seeding immature contractile cells onto the surface of a three dimensional fibroblast containing scaffold (3DFCS) to produce a contractile construct; and
(b) culturing the contractile construct under conditions to promote differentiation of the immature contractile cells into mature contractile cells, wherein the mature contractile cells form striations.

In one embodiment, the immature contractile cells are immature cardiomyocytes and the mature contractile cells are mature cardiomyocytes. In other embodiments, the immature contractile cells are immature smooth muscle cells or skeletal muscle cells and the mature contractile cells are mature smooth muscle cells or skeletal muscle cells. In another embodiment, the contractile construct is implanted in a subject in need thereof after culturing. The construct may be implanted prior to onset of cellular contraction and/or patch level contraction; in another embodiment, the contractile construct is implanted after onset of patch level contraction.

In another aspect, the invention provides constructs comprising contractile cells, or progenitors thereof, adhered to a surface of a three dimensional fibroblast containing scaffold (3DFCS), wherein the construct is capable of spontaneous synchronized contractions across the surface of the 3DFCS; and wherein the contractile cells are seeded on the surface of the construct at a density of between $1.3 \times 10^5$ cells/cm$^2$ and $2.95 \times 10^6$ cells/cm$^2$ and the contractile cells are present on the surface of the 3DFCS in a ratio of between about 1:15 and about 6:1 with fibroblasts on the 3DFCS. In one embodiment, the contractile cells comprise a combination of progenitor contractile cells and mature contractile cells. In another embodiment, the progenitor contractile cells and mature contractile cells are present on the construct surface in a ratio of between about 1:2 and about 2:1. In other embodiments, the contractile cells comprise immature cardiomyocytes, mature cardiomyocytes, or combinations thereof. In other embodiments, the immature contractile cells are immature smooth muscle cells or skeletal muscle cells and the mature contractile cells are mature smooth muscle cells or skeletal muscle cells. In another embodiment, the contractile cells form striations on the construct.

In a further aspect, the invention provides methods for treating a disorder characterized by a lack of functioning contractile cells, comprising contacting a patient with a contractile cell-based disorder with an amount effective to treat the disorder with the construct of any embodiment or combination of embodiments of the invention. In one embodiment, the contractile cells comprise immature cardiomyocytes, mature cardiomyocytes, or combinations thereof, and the method comprises contacting the heart of a subject suffering from such a disorder with an amount effective of the construct to treat the disorder, where the disorder may include, but is not limited to, ischemia-induced heart failure, chronic heart failure (CHF), ischemia without heart failure, cardiomyopathy, dilated cardiomyopathy (DCM), cardiac arrest, congestive heart failure, stable angina, unstable angina, myocardial infarction, coronary artery disease, valvular heart disease, ischemic heart disease, reduced ejection fraction, reduced myocardial perfusion, maladaptive cardiac remodeling, maladaptive left ventricle remodeling, reduced left ventricle function, left heart failure, right heart failure, backward heart failure, forward heart failure, systolic dysfunction, diastolic dysfunction, increased or decreased systemic vascular resistance, low-output heart failure, high-output heart failure, dyspnea on exertion, dyspnea at rest, orthopnea, tachypnea, paroxysmal nocturnal dyspnea, dizziness, confusion, cool extremities at rest, exercise intolerance, easy fatigue ability, peripheral edema, nocturia, ascites, hepatomegaly, pulmonary edema, cyanosis, laterally displaced apex beat, gallop rhythm, heart murmurs, parasternal heave, and pleural effusion.

In one embodiment, the construct is attached to the epicardium of the subject. In other embodiments, the construct is non-contracting at the time of contacting with the epicardiutn, or the construct is contracting at the time of contacting with the epicardium. In a further embodiment, the treating comprises one or more of improving left ventricular function, decreasing left ventricular end diastolic pressure (EDP), improving myocardial perfusion, repopulating of the heart's wall with cardiomyocytes, reversing maladaptive left ventricle remodeling in CHF subjects, improvement in diastolic function such as left ventricular passive filling, active filling, chamber compliance and parameters of heart failure including, but not limited to increasing E' (minis), decreasing E/E', increasing LV dP/dt (mmHg/sec) and decreasing Tau (msec). In another embodiment, the cardiomyocytes on the construct electrically integrate into the patient's native myocardium.

In a further embodiment, the contractile cells comprise immature skeletal muscle cells, immature smooth muscle cells, mature skeletal muscle cells, mature smooth muscle cells, or combinations thereof, and the methods involve treating any disorder that may benefit from enhancing, repairing, or restoring skeletal muscle tissue and/or smooth muscle tissue, by contacting a patient with the disorder with an amount effective to treat the disorder of the construct.

In another aspect, the invention provides methods for drug screening, comprising contacting the construct of any embodiment or combination of embodiments of the invention with a compound of interest and determining an effect of the compound on one or more characteristics of the construct. In one embodiment, method comprises culturing the construct under conditions to promote contraction of the construct prior to contacting the construct with the compound of interest. In another embodiment, the effect of the compound on one or more of contraction displacement, contraction rate, contraction synchronicity, and contraction velocity is determined.

DETAILED DESCRIPTION OF THE INVENTION

Figures 1D, 1E:
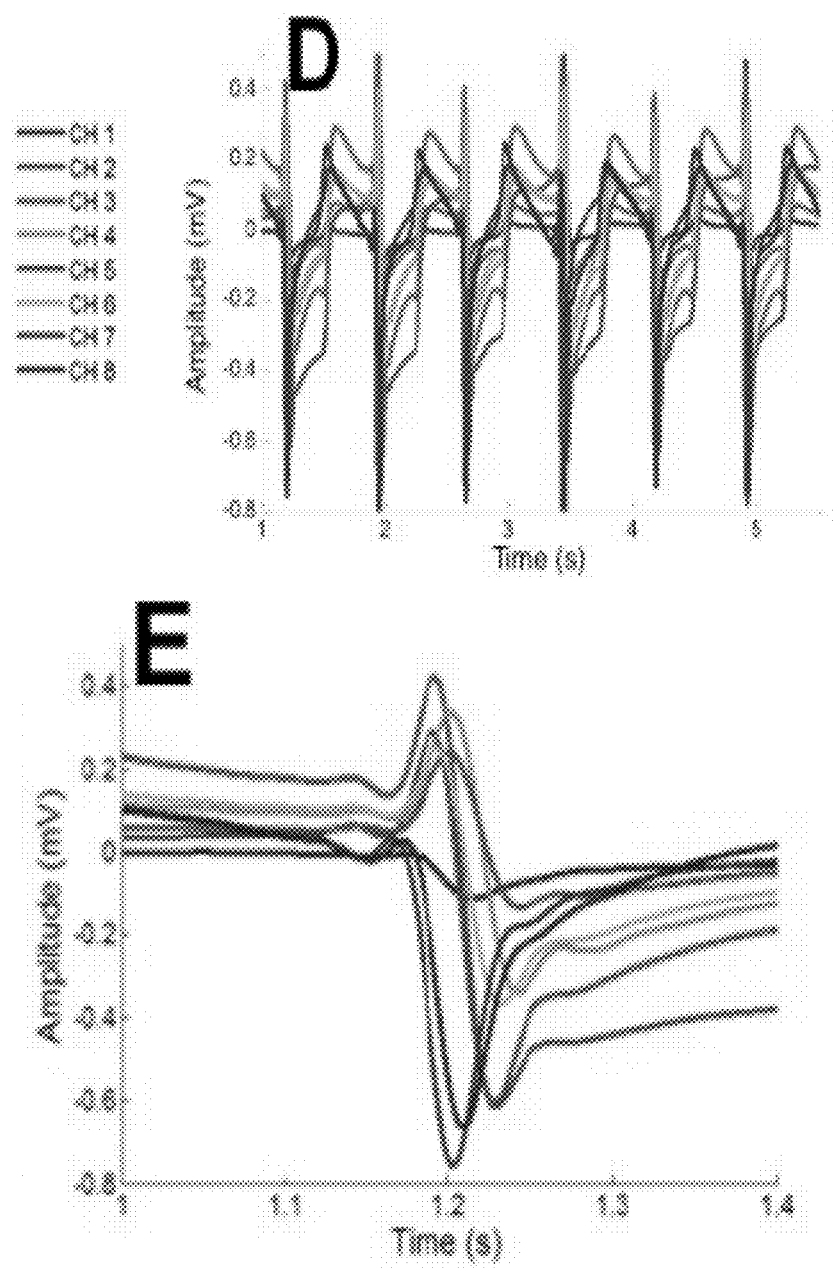
FIG. 1. Electrical activation mapping was performed on the neonatal cardiomyocytes (NCM)-3 dimensional fibroblast construct (3DFC) in tissue culture 5 days after co-culturing using a custom designed multi-electrode array (MEA) with 18 recording sites spaced 500 μm apart (A). Recordings were performed from 10 electrodes; each recording site was numbered sequentially as channel 1-10 (B). The electrical activation of the patch showed consistent beat-to-beat activation as shown in 7 sec interval displaying the peak transverse conduction voltage for each individual channel (C). The amplitude is shown with all channels superimposed in a beat-to-beat sequence (D) and during a single activation (E). The amplitude was recorded as 0.03 to 0.42 and −0.13 to −0.75 mV (D & E).

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, $2^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

As used herein, the term "about" means+/−5% of the recited parameter.

All embodiments of any aspect of the invention can be used in combination, unless the context clearly dictates otherwise.

In a first aspect, the present invention provides constructs comprising contractile cells, adhered to a surface of a three dimensional fibroblast containing scaffold (3DFCS), wherein the construct is capable of spontaneous synchronized contractions across the surface of the 3DFCS; and wherein the contractile cells are seeded on the surface of the construct at a density of between $1.3 \times 10^5$ cells/cm$^2$ and $2.95 \times 10^6$ cells/cm$^2$ and the contractile cells are present on the surface of the 3DFCS in a ratio of between about 1:15 and about 6:1 with fibroblasts on the 3DFCS.

The constructs of the invention can be used for therapeutic and drug screening uses as described herein. The constructs are demonstrated in the examples to provide a functional benefit when implanted in a rodent model of congestive heart failure, and to be electrically stable when implanted.

As used herein, a "three dimensional fibroblast construct" is a construct comprising fibroblasts grown on a three-dimensional substrate comprising a biocompatible, non-living material formed into a three-dimensional structure having interstitial spaces bridged by the cells in the construct. It will be understood that the 3DFC may contain cell types in addition to fibroblasts as appropriate for a given purpose. For example, the 3DFC may also comprise other stromal cells, including but not limited to endothelial cells. See, for example, published US patent application US2009/0269316 and U.S. Pat. No. 4,963,489, both incorporated by reference herein in their entirety.

The fibroblasts and other cells may be fetal or adult in origin, and may be derived from convenient sources such as skin, cardiac muscle, smooth muscle, skeletal muscle, liver, pancreas, brain, adipose tissue (fat) etc. Such tissues and or organs can be obtained by appropriate biopsy or upon autopsy. In alternative embodiments for all aspects of the invention, the fibroblasts and other cells are human cells. In an alternative embodiment for all aspects of the invention, the 3DFC is a matrix-embedded human dermal construct of newborn dermal fibroblasts cultured in vitro onto a bioabsorbable mesh to produce living, metabolically active tissue. The fibroblasts proliferate across the mesh and secrete a large variety of growth factors and cytokines, including human dermal collagen, fibronectin, and glycosaminoglycans (GAGs), embedding themselves in a self-produced dermal matrix, in culture the fibroblasts produce angiogenic growth factors: VEGF (vascular endothelial growth factor), HGF (hepatocyte growth factor), bFGF (basic fibroblast growth factor), and angiopoietin-1 (See, for example, J. Anat. (2006) 209, pp 527-532).

Any suitable 3DFCS can be used, including but not limited to any and all scaffolds—synthetic, biological, degradable, non-degradable, porous, etc., which may include one or more of woven, bonded, spun, printed, degradable, non-degradable, allogeneic, autologous, xenograft, pores (even spacing, uneven spacing, varying sizes), extracellular matrix, etc.

The three-dimensional support framework may be of any material and/or shape that: (a) allows cells to attach to it (or can be modified to allow cells to attach to it); and (b) allows cells to grow in more than one layer. A number of different materials may be used to form the framework, including but not limited to: nylon (polyamides), dacron (polyesters), polystyrene, polypropylene, polyacrylates, polyvinyl compounds (e.g., polyvinylchloride; PVC), polycarbonate, polytetrafluorethylene (PTFE; TEFLON), thermanox (TPX), nitrocellulose, cotton, polyglycolic acid (PGA), cat gut sutures, cellulose, gelatin, dextran, etc. Any of these materials may be woven into a mesh to form the three-dimensional framework. Certain materials, such as nylon, polystyrene, etc., are poor substrates for cellular attachment. When these materials are used as the three-dimensional support framework, it is advisable to pre-treat the framework prior to inoculation of fibroblasts and other stromal cells in order to enhance their attachment to the framework. For example, prior to inoculation with fibroblasts and other stromal cells, nylon screens could be treated with 0.1 M acetic acid, and incubated in polylysine, fetal bovine serum, and/or collagen to coat the nylon. Polystyrene could be similarly treated using sulfuric acid.

When the 3DFC is to be implanted directly in vivo, it may be preferable to use biodegradable materials such as PGA, catgut suture material, collagen, polylactic acid, or hyaluronic acid. For example, these materials may be woven into a three-dimensional framework such as a collagen sponge or collagen gel. Where the cultures are to be maintained for long periods of time or cryopreserved, non-degradable materials such as nylon, dacron, polystyrene, polyacrylates, polyvinyls, teflons, cotton, etc. may be preferred. A convenient nylon mesh which could be used in accordance with the invention is a nylon filtration mesh having an average pore size of 140 µm and an average nylon fiber diameter of 90 µm (#3-210/36, Tetko, Inc., N.Y.).

Any suitable contractile cell can be used, including but not limited to smooth muscle cells, skeletal muscle cells, and cardiac muscle cells, or combinations thereof.

The contractile cells can be derived from any source, including but not limited to fetal tissue, newborn tissue, adult tissues, derived from stem, progenitor cell populations, embryonic cells or reprogrammed somatic cells via induced pluripotent stem cells (iPSC) such as through viral, mRNA, episomal vectors etc. The contractile cells may be fully mature contractile cells, or may be immature cells for a specific contractile cell pathway, or combinations thereof. The cells may be from any suitable organism, such as rodent or primate cells, such as human cells. The cells can be derived from male or female subjects, or cells from male and female subjects can be combined.

In one alternative embodiment, the 3DFC comprises a patch, with the cells seeded onto a top portion of the patch, in this embodiment, the bottom portion of the patch can be attached to a surface of interest, such as the heart.

In one embodiment, the contractile cells are present on the surface of the 3DFCS in a ratio between about 1:10 and about 4:1 fibroblasts. In another embodiment, the contractile cells are present on the surface of the construct in a ratio between about 1:3 and about 1.2:1 fibroblasts. In various further embodiments, the contractile cells of any embodiment or combination of embodiments are present on the surface of the construct in a ratio between about 4:20 and about 1.2:1, about 1:4 and about 1.2:1, about 6:20 and about 1.2:1, about 7:20 and about 1.2:1, about 2:5 and about 1.2:1, about 9:20 and about 1.2:1, about 1:2 and about 1.2:1, about 11:20 and about 1.2:1, about 3:5 and about 1.2:1, about 13:20 and about 1.2:1, about 7:10 and about 1.2:1, about 3:4 and about 1.2:1, about 4:5 and about 1.2:1, about 17:20 and about 1.2:1, about 9:10 and about 1.2:1, about 19:20 and about 1.2:1, and about 1:1 and about 1.2:1, compared to fibroblasts.

In one embodiment, the contractile cells are seeded on the surface of the construct at a density of between $2\times10^5$ cells/cm$^2$ and $2.95\times10^6$ cells/cm$^2$. In another embodiment, the contractile cells are seeded on the surface of the construct at a density of between $2\times10^6$ cells/cm$^2$ and $2.5\times10^6$ cells/cm$^2$. In various further embodiments, the contractile cells are seeded on the surface of the construct at a density of between $2\times10^5$ cells/cm$^2$ and $2.95\times10^6$ cells/cm$^2$; $5\times10$ cells/cm$^2$ and $2.95\times10^6$ cells/cm$^2$; $1\times10^6$ cells/cm$^2$ and $2.95\times10^6$ cells/cm$^2$; $1.5\times10^6$ cells/cm and $2.95\times10^6$ cells/cm$^2$ $1.3\times10^5$ cells/cm$^2$ and $2.5\times10^6$ cells/cm$^2$; or $1.3\times10^5$ cells/cm$^2$ and $2\times10^6$ cells/cm$^2$.

In a further embodiment, the contractile cells comprise a combination of immature contractile cells and mature contractile cells. In one such embodiment, the immature contractile cells and mature contractile cells are present on the construct surface in a ratio of between about 1:2 and about 2:1. In other embodiments, the ratio is between about 1:1 and about 2:1; or about 1:1 and about 1:2.

In a further embodiment, the contractile cells are engineered to reduce or eliminate expression of CD40 and/or HLA. This embodiment provides cells that have been selected for a diminished immune profile, which would allow for better retention of the transplanted cells in the host, which is especially suitable for allogeneic transplantation.

In a further embodiment, the contractile cells are derived from inducible pluripotent stem cells (iPSCs). In non-limiting embodiments, the mature contractile cells may be generated on the construct using the methods of the invention described herein.

In one embodiment, the contractile cells comprise immature cardiomyocytes.

As used herein, an "immature cardiomyocytes" lacks visible sarcomeres In various embodiments, compared to "mature cardiomyocytes" possesses one or more of the following properties:

Morphologically smaller in cell size;
Decreased myofibril density;
Electrophysiologically stunted/diminished action potential amplitudes;
Reduced gene and/or protein expression of MYH7 (Beta myosin heavy chain), MYH6 (alpha myosin heavy chain), SCN5A, GJA1 (connexin 43), HCN4 (hyperpolarization-activated K+channels), KCNJ2 (inward rectifier potassium ion channel), SERCA2a (sarcoendoplasmic reticulum ATPase), alpha actinin, cardiac troponin I (cTnI), Cardiac troponin T (cTnT)

In another embodiment, the contractile cells comprise mature cardiomyocytes. As used herein, a "mature cardiomyocytes" possess visible sarcomeres. In various embodiments, compared to "immature cardiomyocytes," a mature cardiomyocytes possesses one or more of the following properties:

Morphologically smaller in cell size;
Decreased myofibril density;
Electrophysiologically stunted/diminished action potential amplitudes;
Reduced gene and/or protein expression of MYH7 (Beta myosin heavy chain), MYH6 (alpha myosin heavy chain), SCN5A, GJA1 (connexin 43), HCN4 (hyperpolarization-activated K+channels), KCNJ2 (inward rectifier potassium ion channel), SERCA2a (sarcoendoplasmic reticulum ATPase), alpha actinin, cardiac troponin (cTnI), Cardiac troponin T (cTnT)

The inventors have shown maturation of immature cardiomyocytes (such as those derived from iPSCs) on the construct, demonstrating that the constructs provides a unique and supportive environment that promotes survival and maturation of the contractile cells, and thus is effective for vivo administration of cells.

In one embodiment, the immature cardiomyocytes and/or the mature cardiomyocytes are seeded on the surface of the construct at a density of between $1.3\times10^5$ cells/cm$^2$ and $2.7\times10^6$ cells/cm$^2$ and the contractile cells are present on the surface of the 3DFCS in a ratio of between about 1:7 and about 3:1 with fibroblasts on the 3DFCS. In another embodiment, the immature cardiomyocytes and/or the mature cardiomyocytes are seeded on the surface of the construct at a total density of between $1.2\times10^6$ cells/cm$^2$ and $2.3\times10^6$ cells/cm$^2$. In various embodiments, the construct comprises a dose range of cardiomyocytes at $2.9\times10^5$ cells/cm$^2$, $1.2\times10^6$ cells/cm$^2$ or $2.3\times10^6$ cells/cm$^2$ for therapeutic use.

In various embodiments, the cardiomyocytes are present on the surface of the 3DFCS in a ratio of between about 1.5:1-1:1.7; 1:1-3:1; 1:15 and 3.5:1; 1:15 and 1.7:1; 1:6 and 3.5:1; 1.6 and 1.5:1; or 1:1.7 and 1.5:1 with fibroblasts on the 3DFCS.

Cardiomyocyte populations may be 100% mature cardiomyocyte or 100% immature cardiomyocytes, 50% mature cardiomyocytes and 50% immature cardiomyocytes, or any suitable variation thereof.

In another embodiment, the contractile cells comprise smooth muscle cells. In one such embodiment, the smooth muscle cells are seeded on the surface of the construct at a density of between $1.2\times10^6$ cells/cm$^2$ and $2.95\times10^6$ cells/cm$^2$ and the smooth muscle cells are present on the surface of the 3DFCS in a ratio of between about 1:15 and about 3.5:1 with fibroblasts on the 3DFCS. In various embodiments, the smooth muscle cells are present on the surface of the 3DFCS in a ratio of between about 1:15 and 3.5:1; 1:15 and 1.7:1; 1:6 and 3.5:1; 2.5:1-6:1; 1.6 and 1.5:1; or 1:1.7 and 1.5:1 with fibroblasts on the 3DFCS.

In various further embodiments, the smooth muscle cells are seeded on the surface of the construct at a density of between $1.3\times10^5$ cells/cm$^2$ and $2.94\times10^6$ cells/cm$^2$; $1.2\times10^6$ cells/cm$^2$ and $2.94\times10^6$ cells/cm$^2$; $1.3\times10^5$ calls/cm$^2$ and $1.2\times10^6$ cells/cm$^2$; or $1.0\times10^6$ cells/cm$^2$ and $1.2\times10^6$ cells/cm$^2$. In another embodiment, the smooth muscle cells are seeded on the surface of the construct at a density of between $1.0\times10^6$ cells/cm$^2$ and $1.2\times10^6$ cells/cm$^2$ and the smooth muscle cells are present on the surface of the 3DFCS in a ratio of between about 1:1.7 and about 1.5:1 with fibroblasts on the 3DFCS.

In a further embodiment, the contractile cells comprise skeletal muscle cells. In one such embodiment, the skeletal muscle cells are seeded on the surface of the construct at a density of between $1.3\times10^5$ cells/cm$^2$ and $2.95\times10^6$ cells/cm$^2$ and the skeletal muscle cells are present on the surface of the 3DFCS in a ratio of between about 1:15 and about 3.5:1 with fibroblasts on the 3DFCS. In various embodiments, the skeletal muscle cells are present on the surface of the 3DFCS in a ratio of between about 1:15 and 3.5:1; 1:15 and 1.7:1; 1:6 and 3.5:1; 1.6 and 1.5:1; or 1:1.7 and 1.5:1 with fibroblasts on the 3DFCS. In various further embodiments, the skeletal muscle cells are seeded on the surface of the construct at a density of between $1.3\times10^5$ cells/cm$^2$ and $2.94\times10^6$ cells/cm$^2$; $1.2\times10^6$ cells/cm$^2$ and $2.94\times10^6$ cells/cm$^2$; $1.3\times10^5$ cells/cm$^2$ and $1.2\times10^6$ cells/cm$^2$; or $1.0\times10^6$ cells/cm$^2$ and $1.2\times10^6$ cells/cm$^2$. In another embodiment, the skeletal muscle cells are seeded on the surface of the construct at a density of between $1.0\times10^5$ cells/cm$^2$ and $12.0\times10^6$ cells/cm$^2$ and the skeletal muscle cells are present on the surface of the 3DFCS in a ratio of between about 1:1.7 and about 1.5:1 with fibroblasts on the 3DFCS.

In one embodiment, the contractile cells of any embodiment or combination of embodiments form striations on the construct, particularly for cardiomyocytes and skeletal muscle embodiments of the constructs. In these embodiments, the contractile cells form repeating sarcomeres, which can be visualized microscopically.

The construct of any embodiment may comprise contractile cells engineered to express any biological pharmacological agents, gene activation, of cell scaffolding, extracellular matrix etc for muscle repair. which may include: pretreatment, preloading, over expression, general drug eluting properties, which may include proteins, amino acid derivatives, polypeptide hormones, steroids, mRNA, DNA, cytokines, growth factors, receptors (intrinsic or modified) pertaining to cells or scaffolding, enzymes, zymogens, viral agents, bacterial agents etc. or any combination of the above.

Exemplary such compounds include, but are not limited to one or more of thymosin beta-4 (TB4), akt murine thymoma viral oncogene homolog (AKT1), stromal cell-derived factor-1 alpha (SDF-1), genes that promote vascularization, and hepatocyte growth factor (HGF).

The constructs of the invention may further comprise any biological pharmacological agents, gene activation, cell scaffolding, extracellular matrix, or incorporation of established vessels capable of surgical or biological integration into the native vasculature.

In another aspect, the present invention provides methods for treating a disorder characterized by a lack of functioning contractile cells, comprising contacting a patient with a contractile cell-based disorder with an amount effective to treat the disorder with the construct of any embodiment or combination of embodiments of the invention. The inventors have shown maturation of immature cardiomyocytes (such as those derived from iPSCs) on the construct, demonstrating that the constructs provide a unique and supportive environment that promotes survival and maturation of the contractile cells, and thus effective for vivo administration of cells. The constructs are demonstrated in the examples to provide a functional benefit when implanted in a rodent model of congestive heart failure, and to be electrically stable when implanted. The inventors have also demonstrated that the human iPSC-derived cardiomyocytes cardiac patches result in up regulation of angiopoietin 1 (ANG-1), Connexin 43 (Cx43), and vascular endothelial growth factor (VEGF) mRNA expression levels after implantation in left ventricular heart tissue.

The constructs of the invention may be implanted by either surgical means (open cavity, minimally invasive, robotically, catheter, etc) and can be implanted/set in place through the application of suture, glues, cellular adhesions, polarization (magnetic), etc. The constructs may be manufactured and cryopreserved before use.

In one embodiment, the contractile cells comprise immature cardiomyocytes, mature cardiomyocytes, or combinations thereof, and wherein the method comprises contacting the heart of a subject suffering from such a disorder with an amount effective of the construct to treat the disorder. In this embodiment, the disorder may include, but is not limited to ischemia-induced heart failure, chronic heart failure (CHF), ischemia without heart failure, cardiomyopathy, dilated cardiomyopathy (DCM), cardiac arrest, congestive heart failure, stable angina, unstable angina, myocardial infarction, coronary artery disease, valvular heart disease, ischemic heart disease, reduced ejection fraction, reduced myocardial perfusion, maladaptive cardiac remodeling, maladaptive left ventricle remodeling, reduced left ventricle function, left heart failure, right heart failure, backward heart failure, forward heart failure, systolic dysfunction, diastolic dysfunction, increased or decreased systemic vascular resistance, low-output heart failure, high-output heart failure, dyspnea on exertion, dyspnea at rest, orthopnea, tachypnea, paroxysmal nocturnal dyspnea, dizziness, confusion, cool extremities at rest, exercise intolerance, easy fatigue ability, peripheral edema, nocturia, ascites, hepatomegaly, pulmonary edema, cyanosis, laterally displaced apex beat, gallop rhythm, heart murmurs, parasternal heave, and pleural effusion.

Thus, the present methods utilize the 3DFC as a delivery system for cell-based therapy using the heart as its own bioreactor to support the engraftment/growth of cells seeded on the 3DFC. The methods of the invention permit covering a larger amount of myocardium as opposed to isolated cell injections, thus addressing one criticism as to why cell injections appear to work better in rodents than humans, i.e., the amount of damaged myocardium needed to treat. Also cells seeded on the 3DFC will not wash out in the circulation as seen with insolated cell injections.

In an alternative embodiment that can be combined with any other embodiments herein, the subject is a mammal, most preferably a human. In a further alternative embodiment that can be combined with any other embodiments herein, the subject is human. In another alternative embodiment, the immature cardiomyocytes, mature cardiomyocytes, or combinations thereof are obtained from the subject.

As used herein, "CHF" is a chronic (as opposed to rapid onset) impairment of the heart's ability to supply adequate blood to meet the body's needs. CHF may be caused by, but is distinct from, cardiac arrest, myocardial infarction, and cardiomyopathy. In one alternative embodiment, the subject suffers from congestive heart failure. In various further alternative embodiments that can be combined with any other embodiments herein, the subject's heart failure comprises left heart failure, right heart failure, backward heart failure (increased venous back pressure), forward heart failure (failure to supply adequate arterial perfusion), systolic dysfunction, diastolic dysfunction, systemic vascular resistance, low-output heart failure, high-output heart failure. In various further alternative embodiments that can be combined with any other embodiments herein, the subject's CHF may be any of Classes I-IV as per the New York Heart Association Functional Classification; more preferably Class III or IV.

Class I: no limitation is experienced in any activities; there are no symptoms from ordinary activities.

Class II: slight, mild limitation of activity; the patient is comfortable at rest or with mild exertion.

Class III: marked limitation of any activity; the patient is comfortable only at rest.

Class IV: any physical activity brings on discomfort and symptoms occur at rest.

In a further alternative embodiment that can be combined with any other embodiments herein, the subject has been diagnosed with CHF according to the New York Heart Association Functional Classification. In a further alternative embodiment that can be combined with any other embodiments herein, the subject is further characterized by one or more of the following: hypertension, obesity, cigarette smoking, diabetes, valvular heart disease, and ischemic heart disease.

As used herein, "treat" or "treating" means accomplishing one or more of the following: (a) reducing the severity of the disorder (ex: treatment of Class IV subject to improve status to Class III for CHF subjects); (b) limiting or preventing development of symptoms characteristic of the disorder; (c) inhibiting worsening of symptoms characteristic of the disorder; (d) limiting or preventing recurrence of symptoms in patients that were previously symptomatic for the disorder. Signs characteristic of CHF include, but are not limited to reduced ejection fraction, reduced myocardial perfusion, maladaptive cardiac remodeling (such as left ventricle remodeling), reduced left ventricle function, dyspnea on exertion, dyspnea at rest, orthopnea, tachypnea, paroxysmal nocturnal dyspnea, dizziness, confusion, cool extremities at rest, exercise intolerance, easy fatigueability, peripheral edema, nocturia, ascites, hepatomegaly, pulmonary edema, cyanosis, laterally displaced apex beat, gallop rhythm, heart murmurs, parasternal heave, and pleural effusion.

In various embodiments, the treating comprises one or more of improving left ventricular function, decreasing left ventricular end diastolic pressure (EDP), improving myocardial perfusion, repopulating of the heart's wall with cardiomyocytes, reversing maladaptive left ventricle remodeling in CHF subjects, improvement in diastolic function such as left ventricular passive filling, active filling, chamber compliance and parameters of heart failure including, but not limited to increasing E' (mm/s), decreasing E/E', increasing LV dP/dt (mmHg/sec) and decreasing Tau (msec).

In one embodiment, the constructs described herein find use in promoting the healing of ischemic heart tissue. The ability of the constructs to promote the healing of an ischemic tissue depends in part, on the severity of the ischemia. As will be appreciated by the skilled artisan, the severity of the ischemia depends, in part, on the length of time the tissue has been deprived of oxygen. Among such activities is the reduction or prevention of the remodeling of ischemic tissue. By "remodeling" herein is meant, the presence of one or more of the following: (1) a progressive thinning of the ischemic tissue, (2) a decrease in the number or blood vessels supplying the ischemic tissue, and/or (3) a blockage in one or more of the blood vessels supplying the ischemic tissue, and if the ischemic tissue comprises muscle tissue, (4) a decrease in the contractibility of the muscle tissue. Untreated, remodeling typically results in a weakening of the ischemic tissue such that it can no longer perform at the same level as the corresponding healthy tissue. Cardiovascular ischemia is generally a direct consequence of coronary artery disease, and is usually caused by rupture of an atherosclerotic plaque in a coronary artery, leading to formation of thrombus, which can occlude or obstruct a coronary artery, thereby depriving the downstream heart muscle of oxygen. Prolonged ischemia can lead to cell death or necrosis, and the region of dead tissue is commonly called an infarct.

In some embodiments, candidate subjects for the methods described herein will be patients with stable angina and reversible myocardial ischemia. Stable angina is characterized by constricting chest pain that occurs upon exertion or stress, and is relieved by rest or sublingual nitroglycerin. Coronary angiography of patients with stable angina usually reveals 50-70% obstruction of at least one coronary artery. Stable angina is usually diagnosed by the evaluation of clinical symptoms and ECG changes. Patients with stable angina may have transient ST segment abnormalities, but the sensitivity and specificity of these changes associated with stable angina are low.

In some embodiments, candidates for the methods described herein will be patients with unstable angina and reversible myocardial ischemia. Unstable angina is characterized by constricting chest pain at rest that is relieved by sublingual nitroglycerin. Anginal chest pain is usually relieved by sublingual nitroglycerin, and the pain usually subsides within 30 minutes. There are three classes of unstable angina severity: class I, characterized as new onset, severe, or accelerated angina; class II, subacute angina at rest characterized by increasing severity, duration, or requirement for nitroglycerin; and class III, characterized as acute angina at rest. Unstable angina represents the clinical state between stable angina and acute myocardial infarction (AMI) and is thought to be primarily due to the progression in the severity and extent of atherosclerosis, coronary artery spasm, or hemorrhage into non-occluding plaques with subsequent thrombotic occlusion. Coronary angiography of patients with unstable angina usually reveals 90% or greater obstruction of at least one coronary artery, resulting in an inability of oxygen supply to meet even baseline myocardial oxygen demand. Slow growth of stable atherosclerotic plaques or rupture of unstable atherosclerotic plaques with subsequent thrombus formation can cause unstable angina. Both of these causes result in critical narrowing of the coronary artery. Unstable angina is usually associated with atherosclerotic plaque rupture, platelet activation, and thrombus formation. Unstable angina is usually diagnosed by clinical symptoms, ECG changes, and changes in cardiac markers.

In some embodiments, candidates for the methods described herein will be human patients with left ventricular dysfunction and reversible myocardial ischemia that are undergoing a coronary artery bypass graft (CABG) procedure, who have at least one graftable coronary vessel and at least one coronary vessel not amenable to bypass or percutaneous coronary intervention.

In some embodiments, application of the construct to an ischemic tissue increases the number of blood vessels present in the ischemic tissue, as measured using laser Doppler imaging (see, e.g., Newton et al., 2002, J Foot Ankle Surg, 41(4):233-7). In some embodiments, the number of blood vessels increases 1%, 2%, 5%; in other embodiments, the number of blood vessels increases 10%, 15%, 20%, even as much as 25%, 30%, 40%, 50%; in some embodiments, the number of blood vessels increase even more, with intermediate values permissible.

In some embodiments, application of the construct to an ischemic heart tissue increases the ejection fraction. In a healthy heart, the ejection fraction is about 65 to 95 percent. In a heart comprising ischemic tissue, the ejection fraction is, in some embodiments, about 20-40 percent. Accordingly, in some embodiments, treatment with the construct results in a 0.5 to 1 percent absolute improvement in the ejection fraction as compared to the ejection fraction prior to treatment. In other embodiments, treatment with the construct results in an absolute improvement in the ejection fraction more than 1 percent. In some embodiments, treatment results in an absolute improvement in the ejection fraction of 1.5%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, or more as compared to the ejection fraction prior to treatment. For example, if the ejection fraction prior to treatment was 40%, then following treatment ejection fractions between 41% to 59% or more are observed in these embodiments. In still other embodiments, treatment with the construct results in an improvement in the ejection fraction greater than 10% as compared to the ejection fraction prior to treatment.

In some embodiments, application of the construct to an ischemic heart tissue increases one or more of cardiac output (CO) (increases of up to 55% or more relative to pre-status treatment), left ventricular end diastolic volume index (LVEDVI), left ventricular end systolic volume index (LVESVI), and systolic wall thickening (SWT). These parameters are measured by art-standard clinical procedures, including, for example, nuclear scans, such as radionuclide ventriculography (RNV) or multiple gated acquisition (MUGA), and X-rays.

In some embodiments, application of the construct to an ischemic heart tissue causes a demonstrable improvement in the blood level of one or more protein markers used clinically as indicia of heart injury, such as creatine kinase (CK), serum glutamic oxalacetic transaminase (SGOT), lactic dehydrogenase (LDH) (see, e.g., U.S. Publication 2005/0142613), troponin I and troponin T can be used to diagnose heart muscle injury (see, e.g., U.S. Publication 2005/0021234). In yet other embodiments, alterations affecting the N-terminus of albumin can be measured (see, e.g., U.S. Publications 2005/0142613, 2005/0021234, and 2005/

0004485; the disclosures of which are incorporated herein by reference in their entireties).

Additionally, the constructs can be used with therapeutic devices used to treat heart disease including heart pumps, endovascular stents, endovascular stent grafts, left ventricular assist devices (LVADs), biventricular cardiac pacemakers, artificial hearts, and enhanced external counterpulsation (EECP).

In a further alternative embodiment that can be combined with any other embodiments herein, the treating results in production of new cardiomyocytes and new blood vessels in the subject. In a further alternative embodiment that can be combined with any other embodiments herein, the treating results in improvement of left ventricular function, fall in end diastolic pressure (EDP) (reduction of up to 50-60% or more relative to pre-status treatment), myocardial perfusion, repopulation of the anterior wall with cardiomyocytes, and/or reversing maladaptive left ventricle remodeling in the subject.

In one non-limiting alternative embodiment in which a synchronously beating construct is placed on the heart to aid in contraction of the left ventricle, beneficial treatment can be demonstrated by an improvement in ejection fraction. In a further non-limiting alternative embodiment, a non-beating construct is placed on the heart and then spontaneously begins beating on the heart to aid in contraction of the heart.

The construct can be contacted with the heart in any suitable way to promote attachment. The construct may be attached to various locations on the heart, including the epicardium, myocardium and endocardium, most preferably the epicardium. Means for attachment include, but are not limited to, direct adherence between the construct and the heart tissue, biological glue, suture, synthetic glue, laser dyes, or hydrogel. A number of commercially available hemostatic agents and sealants include SURGICAL® (oxidized cellulose), ACTIFOAM® (collagen), FIBRX® (light-activated fibrin sealant), BOHEAL® (fibrin sealant), FIBROCAPS® (dry powder fibrin sealant), polysaccharide polymers p-GlcNAc (SYVEC® patch; Marine Polymer Technologies), Polymer 27CK (Protein Polymer Tech.). Medical devices and apparatus for preparing autologous fibrin sealants from 120 ml of a patient's blood in the operating room in one and one-half hour are also known (e.g. Vivostat System).

In an alternative embodiment of the invention utilizing direct adherence, the construct is placed directly onto the heart and the product attaches via natural cellular attachment. In a further alternative embodiment, the construct is attached to the heart using surgical glue, preferably biological glue such as a fibrin glue. The use of fibrin glue as a surgical adhesive is well known. Fibrin glue compositions are known (e.g., see U.S. Pat. Nos. 4,414,971; 4,627,879 and 5,290,552) and the derived fibrin may be autologous (e.g., see U.S. Pat. No. 5,643,192). The glue compositions may also include additional components, such as liposomes containing one or more agent or drug (e.g., see U.S. Pat. Nos. 4,359,049 and 5,605,541) and include via injection (e.g., see U.S. Pat. No. 4,874,368) or by spraying (e.g., see U.S. Pat. Nos. 5,368,563 and 5,759,171). Kits are also available for applying fibrin glue compositions (e.g., see U.S. Pat. No. 5,318,524).

In another embodiment, a laser dye is applied to the heart, the construct, or both, and activated using a laser of the appropriate wavelength to adhere to the tissues. In alternative embodiments, the laser dye has an activation frequency in a range that does not alter tissue function or integrity. For instance, 800 nm light passes through tissues and red blood cells. Using indocyan green (ICG) as the laser dye, laser wavelengths that pass through tissue may be used. A solution of 5 mg/ml of ICG is painted onto the surface of the three-dimensional stromal tissue (or target site) and the ICG binds to the collagen of the tissue. A 5 ms pulse from a laser emitting light with a peak intensity near 800 nm is used to activate the laser dye, resulting in the denaturation of collagen which fuses elastin of the adjacent tissue to the modified surface.

In another embodiment, the construct is attached to the heart using a hydrogel. A number of natural and synthetic polymeric materials are sufficient for forming suitable hydrogel compositions. For example, polysaccharides, e.g., alginate, may be crosslinked with divalent cations, polyphosphazenes and polyacrylates are crosslinked ionically or by ultraviolet polymerization (U.S. Pat. No. 5,709,854). Alternatively, a synthetic surgical glue such as 2-octyl cyanoacrylate ("DERMABOND™", Ethicon, Inc., Somerville, N.J.) may be used to attach the three-dimensional stromal tissue.

In an alternative embodiment of the present invention, the construct is secured to the heart using one or more sutures, including, but not limited to, 5-O, 6-O and 7-O proline sutures (Ethicon Cat. Nos. 8713H, 8714H and 8701H), poliglecaprone, polydioxanone, polyglactin or other suitable non-biodegradable or biodegradable suture material. When suturing, double armed needles are typically, although not necessarily, used.

In another embodiment, the 3DFC is grown in a bioreactor system (e.g., U.S. Pat. Nos. 5,763,267 and 5,843,766) in which the framework is slightly larger than the final tissue-engineered product. The final product contains a border, one edge, flap or tab of the scaffold material, which is used as the site for application of the biological/synthetic glue, laser dye or hydrogel. In alternative embodiments, the scaffold weave may be used as an attachment for suturing or microsuturing.

As used herein, the phrase "an amount effective" means an amount of the construct that will be effective to treat the disorder, as discussed herein. As will be clear to those of skill in the art, the methods comprise the use of one or more of the recited constructs to treat disorders characterized by a lack of functioning cardiomyocytes. In one embodiment, the method comprises contacting the heart with an amount of one or more constructs that serves to cover one or more ischemic regions of the heart, preferably all ischemic regions of the heart. The construct is used in an amount effective to promote tissue healing and/or revascularization of weakened or damaged heart tissue in an individual diagnosed with a disorder characterized by a lack of functioning cardiomyocytes. The amount of the construct administered, depends, in part, on the severity of the disorder, whether the construct is used as an injectable composition (see, US20060154365, incorporated herein by reference in its entirety), the concentration of the various growth factors and/or Wnt proteins present, the number of viable cells comprising the construct, and/or ease of access to the heart tissue(s) being treated. Determination of an effective dosage is well within the capabilities of those skilled in the art. Suitable animal models, such as the canine model described in US 20060292125 (incorporated by reference herein in its entirety) can be used for testing the efficacy of the dosage on a particular tissue of the heart.

As used herein "dose" refers to the number of cohesive pieces of construct applied to the heart of an individual diagnosed with congestive heart failure. A typical cohesive piece of construct is approximately 35 $cm^2$. As will be appreciated by those skilled in the art, the absolute dimensions of the cohesive piece can vary, as long it comprises a sufficient number of cells to promote healing of weakened or damaged heart tissue in an individual diagnosed with a disorder characterized by a lack of functioning cardiomyocytes. Thus, cohesive pieces suitable for use in the methods described herein can range in size from 15 cm² to 50 cm².

The application of more than one cohesive piece of construct can be used to increase the area of the heart treatable by the methods described herein. For example, in embodiments using a two pieces of cohesive construct, the treatable area is approximately doubled in size. In embodiments using three cohesive pieces of construct, the treatable area is approximately tripled in size. In embodiments using four cohesive pieces of construct, the treatable area is approximately quadrupled in size. In embodiments using five cohesive pieces of construct, the treatable area is approximately five-fold, i.e. from 35 cm² to 175 cm².

In some embodiments, one cohesive piece of construct is attached to a region of the heart in an individual diagnosed with a disorder characterized by a lack of functioning cardiomyocytes.

In other embodiments, two cohesive pieces of construct are attached to a region of the heart in an individual diagnosed with a disorder characterized by a lack of functioning cardiomyocytes.

In other embodiments, three cohesive pieces of construct are attached to a region of the heart in an individual diagnosed with a disorder characterized by a lack of functioning cardiomyocytes.

In other embodiments, four, five, or more cohesive pieces of construct are attached to a region of the heart in an individual diagnosed with a disorder characterized by a lack of functioning cardiomyocytes.

In embodiments in which two or more cohesive pieces of construct are administered, the proximity of one piece to another can be adjusted, depending in part on, the severity of the disorder characterized by a lack of functioning cardiomyocytes, the extent of the area being treated, and/or ease of access to the heart tissue(s) being treated. For example, in some embodiments, the pieces of 3DFC can be located immediately adjacent to each other, such that one or more edges of one piece contact one or more edges of a second piece. In other embodiments, the pieces can be attached to the heart tissue such that the edges of one piece do not touch the edges of another piece. In these embodiments, the pieces can be separated from each other by an appropriate distance based on the anatomical and/or disease conditions presented by the subject. Determination of the proximity of one piece to another, is well within the capabilities of those skilled in the art, and if desired can be tested using suitable animal models, such as the canine model described in US20060292125.

In embodiments that comprise a plurality of pieces of construct, some, or all of the pieces can be attached to the same or different areas of the heart.

In embodiments that comprise a plurality of pieces of construct, the pieces are simultaneously attached, or concurrently attached to the heart.

In some embodiments, the construct pieces are administered over time. The frequency and interval of administration depends, in part, on the severity of the disorder, whether the 3DFC is used as an injectable composition (see, US20060154365, incorporated herein by reference in its entirety), the concentration of the various growth factors and/or Wnt proteins present, the number of viable cells comprising the 3DFC, and/or ease of access to the heart tissue(s) being treated. Determination of the frequency of administration and the duration between successive applications is well within the capabilities of those skilled in the art, and if desired, can be tested using suitable animal models, such as the canine model described in US20060292125.

In a further alternative embodiment, one or more construct is contacted with the left ventricle. In a further alternative embodiment, the one or more constructs cover the entire heart.

In embodiments that comprise a plurality of pieces of construct, some, or all of the pieces can be attached to the area comprising the heart. In other embodiments, one or more of the construct pieces can be attached to areas that do not comprise damaged myocardium. For example, in some embodiments, one piece can be attached to an area comprising ischemic tissue and a second piece can be attached to an adjacent area that does not comprise ischemic tissue. In these embodiments, the adjacent area can comprise damaged or defective tissue. "Damaged," or "defective" tissue as used herein refer to abnormal conditions in a tissue that can be caused by internal and/or external events, including, but not limited to, the event that initiated the ischemic tissue. Other events that can result in ischemic, damaged or defective tissue include disease, surgery, environmental exposure, injury, aging, and/or combinations thereof.

In embodiments that comprise a plurality of pieces of cultured three-dimensional tissue, the construct pieces can be simultaneously attached, or concurrently attached to an ischemic tissue.

The construct can be contracting (cell level, patch (i.e.: construct) level, or both) or non-contracting at the time of contacting with the epicardium. Contractions of the constructs are described in two ways: 1) cellular contraction and 2) patch level contraction. In cellular level contractions, the seeded contractile cells are contractile in a synchronized and spontaneous nature but are not capable of moving the 3DFC; a microscope is required for visualization. Patch level contractions develop after the cells have organized and aligned and result in movement or contraction of the entire patch on a gross level, not requiring any microscopy for visualization.

In one embodiment, the cardiomyocytes on the construct electrically integrate into the patient's native myocardium. This embodiment helps to improve electrical activity in the heart, including but not limited to maintaining recipient in normal sinus rhythm, without induction of dysrhythmias including but not limited to ventricular tachycardia, and ventricular fibrillation.

The methods may further comprise systemic administration of cytokines to the subject, including but not limited to Insulin like growth factor (IGF), Hepatic Growth Factor (HGF), and Stromal cell-derived factor a (SDF-1a).

The methods and compositions described herein can be used in combination with conventional treatments, such as the administration of various pharmaceutical agents and surgical procedures. For example, in some embodiments, the cultured three-dimensional tissue is administered with one or more of the medications used to treat a disorder characterized by a lack of functioning cardiomyocytes. Medications suitable for use in the methods described herein include angiotensin-converting enzyme (ACE) inhibitors (e.g., enalapril, lisinopril, and captopril), angiotensin II (A-II) receptor blockers (e.g., losartan and valsartan), diuretics (e.g., bumetanide, furosemide, and spironolactone), digoxin, beta blockers, and nesiritide.

Additionally, the constructs can be used with other options used to treat a disorder characterized by a lack of functioning cardiomyocytes, including heart pumps, also referred to as left ventricular assist devices (LVADs), biventricular cardiac pacemakers, cardiac wrap surgery, artificial hearts, and enhanced external counterpulsation (EECP), and cardiac wrap surgery (see, e.g., U.S. Pat. Nos. 6,425,856, 6,085,754, 6,572,533, and 6,730,016, the contents of which are incorporated herein by reference).

In some embodiments, the construct is used in conjunction with cardiac wrap surgery. In these embodiments, a flexible pouch or jacket is used to deliver and/or attach the construct, which can be placed inside or embedded within the pouch prior to placement over the damaged or weakened heart tissue. In other embodiments, the pouch and the 3DFC can be joined together. For example, the pouch and the construct can be joined together using a stretchable stitch assembly. In other embodiments, the construct can be configured to comprise threads useful for joining the framework to the pouch. U.S. Pat. Nos. 6,416,459, 5,702,343, 6,077,218, 6,126,590, 6,155,972, 6,241,654, 6,425,856, 6,230,714, 6,241,654, 6,155,972, 6,293,906, 6,425,856, 6,085,754, 6,572,533, and 6,730,016 and U.S. Patent Publication Nos. 2003/0229265, and 2003/0229261, the contents of which are incorporated herein by reference, describe various embodiments of pouches and jackets, e.g., cardiac constraint devices, that can be used to deliver and/or attach the construct.

In some embodiments, other devices, in addition to the construct are attached to the pouch, e.g., electrodes for defibrillation, a tension indicator for indicating when the jacket is adjusted on the heart to a desired degree of tensioning, and used in the methods and compositions described herein. See, e.g., U.S. Pat. Nos. 6,169,922 and 6,174,279, the contents of which are incorporated herein by reference.

A number of methods can be used to measure changes in the functioning of the heart in subjects before and after attachment of the construct. For example, an echocardiogram can be used to determine the capacity at which the heart is pumping. The percentage of blood pumped out of the left ventricle with each heartbeat is referred to as the ejection fraction. In a healthy heart, the ejection fraction is about 60 percent, in an individual with chronic heart failure caused by the inability of the left ventricle to contract vigorously, i.e., systolic heart failure, the ejection fraction is usually less than 40 percent. Depending on the severity and cause of the heart failure, ejection fractions typically range from less than 40 percent to 15 percent or less. An echocardiogram can also be used to distinguish between systolic heart failure and diastolic heart failure, in which the pumping function is normal but the heart is stiff.

In some embodiments, echocardiograms are used to compare the ejection fractions before and following treatment with the construct. In certain embodiments, treatment with the construct results in improvements in the ejection fraction between 3 to 5 percent. In other embodiments, treatment with the construct results in improvements in the ejection fraction between 5 to 10 percent. In still other embodiments, treatment with the construct results in improvements in the ejection fraction greater than 10 percent.

Nuclear scans, such as radionuclide ventriculography (RNV) or multiple gated acquisition (MUGA) scanning can be used to determine how much blood the heart pumps with each beat. These tests are done using a small amount of dye injected in the veins of an individual A special camera is used to detect the radioactive material as it flows through the heart. Other tests include X-rays and blood tests. Chest X-rays can be used to determine the size of the heart and if fluid has accumulated in the lungs. Blood tests can be used to check for a specific indicator of congestive heart failure, brain natriuretic peptide (BNP). BNP is secreted by the heart in high levels when it is overworked. Thus, changes in the level of BNP in the blood can be used to monitor the efficacy of the treatment regime.

In a further aspect, the present invention provides kits for treating CHF, comprising a suitable construct as disclosed above and a means for attaching the construct to the heart or organ. The means for attachment may include any such attachment device as described above, for example, a composition of surgical glue, hydrogel, or preloaded prolene needles for microsuturing.

In another embodiment, the contractile cells comprise immature skeletal muscle cells, immature smooth muscle cells, mature skeletal muscle cells, mature smooth muscle cells, or combinations thereof. While the methods have been demonstrated with cardiac muscle cells, these are exemplary of the full range of contractile cells that can be used to provide an effective drug screening system to assess how drug candidates will work in vivo. In this aspect, the methods may comprise treating any disorder that may benefit from enhancing, repairing, or restoring skeletal muscle tissue and/or smooth muscle tissue, comprising contacting a patient with the disorder with an amount effective to treat the disorder with the construct. Exemplary such disorders include, but are not limited to, neuromuscular, degenerative, inflammatory, autoimmune muscle diseases and or any form of injury such as but not limited to trauma which may include vascular disorders (peripheral artery disease, atherosclerosis, aneurysms, etc.), respiratory diseases (chronic obstructive pulmonary disease, diaphragmatic/hemidiaphragmatic hernia (which may include Bochdalek or congenital diaphragmatic hernia), eventration of the diaphragm, etc.), hernias (inguinal, ventral, spigellian, umbilical, Bochdalek, hiatal, Morgagni, etc.), and any form of injury including sports injuries, burns, posttraumatic, war injuries, muscle wasting etc. that may be the result of blunt force and/or penetrating trauma, etc. or any combination of such.

In another aspect, the invention provides methods for drug screening, comprising contacting the construct of any embodiment or combination of embodiments of the invention with a compound of interest and determining an effect of the compound on one or more characteristics of the construct.

In this aspect, the constructs of the invention can be used for drug screening. The inventors have shown maturation of immature cardiomyocytes (such as those derived from iPSCs) on the construct. Thus, the constructs of the invention offer tissue-like development and signaling. This is significant because drug development companies want to test drugs on the most mature cells possible. Current iPSC (immature) cardiomyocytes do not display full maturation. Our data show that when the iPSC cardiomyocytes are cultured on the constructs of the invention, they mature (i.e.: into mature cardiomyocytes) as opposed to the case in standard culture of iPSC cardiomyocytes. In one embodiment, the methods of this aspect are used with the cardiomyocytes constructs of the invention. While the methods have been demonstrated with cardiac muscle cells, these are exemplary of the full range of contractile cells that can be used to provide an effective drug screening system to assess how drug candidates will work in vivo.

In this aspect, the method may comprise culturing the construct under conditions to promote contraction of the construct prior to contacting the construct with the compound of interest. In this embodiment, the patch is cultured until cell and/or patch level contractions (preferably patch level contractions) are generated, and then drug added. The patch's contractions (displacement, contraction rates/peak frequency, synchronicity, rate, velocity, action potential, beat/contraction pattern, etc.) would be recorded and analyzed in. In one embodiment, the contractile cells may have inherent genetic deficiencies, such as long QT. Suitable culture techniques can be determined by one of skill in the art, based on the disclosure herein and the intended purpose of the assay to be carried out.

In a further aspect, the invention provides methods for preparing a contractile construct, comprising (a) seeding immature contractile cells onto the surface of a three dimensional fibroblast containing scaffold (3DFCS) to produce a contractile construct; and (b) culturing the contractile construct under conditions to promote differentiation of the immature contractile cells into mature contractile cells, wherein the mature contractile cells form striations.

The inventors have surprisingly discovered that fibroblast-containing constructs enhance/promote maturation of immature contractile cells into more mature cells as defined morphologically or via gene or protein expression thus greatly facilitating preparation of contractile constructs that can be used, for example, for transplantation in therapeutic preparations or for drug screening assay, as described herein.

In one embodiment, the immature contractile cells are immature cardiomyocytes and the mature contractile cells are mature cardiomyocytes, as defined herein. In another embodiment, the immature contractile cells are immature smooth muscle cells and the mature contractile cells are mature smooth muscle cells. In a further embodiment, the immature contractile cells are immature skeletal muscle cells and the mature contractile cells are mature skeletal muscle cells.

In one embodiment, the contractile cells are seeded on the surface of the 3DFCS in a ratio between about 1:15 and about 6:1, or about 1:10 and about 4:1 fibroblasts. In another embodiment, the contractile cells are seeded on the surface of the construct in a ratio between about 1:3 and about 1.2:1 fibroblasts. In various further embodiments, the contractile cells of any embodiment or combination of embodiments are seeded on the surface of the construct in a ratio between about 4:20 and about 1.2:1, about 1:4 and about 1.2:1, about 6:20 and about 1.2:1, about 7:20 and about 1.2:1, about 2:5 and about 1:2:1, about 9:20 and about 1.2:1, about 1:2 and about 1.2:1, about 11:20 and about 1.2:1, about 3:5 and about 1.2:1, about 13:20 and about 1.2:1, about 7:10 and about 1.2:1, about 3:4 and about 1.2:1, about 4:5 and about 1.2:1, about 17:20 and about 1.2:1, about 9:10 and about 1.2:1, about 19:20 and about 1.2:1, and about 1:1 and about 1.2:1, compared to fibroblasts.

In one embodiment, the contractile cells are seeded on the surface of the construct at a density of between $1.3 \times 10^5$ cells/cm$^2$ and $2.95 \times 10^6$ cells/cm$^2$ or between $2 \times 10^5$ cells/cm$^2$ and $2.95 \times 10^6$ cells/cm$^2$. In another embodiment, the contractile cells are seeded on the surface of the construct at a density of between $2 \times 10^6$ cells/cm$^2$ and $2.5 \times 10^6$ cells/cm$^2$. In various further embodiments, the contractile cells are seeded on the surface of the construct at a density of between $2 \times 10^5$ cells/cm$^2$ and $2.95 \times 10^6$ cells/cm$^2$; $5 \times 10^5$ cells/cm$^2$ and $2.95 \times 10^6$ cells/cm$^2$; $1 \times 10^6$ cells/cm$^2$ and $2.95 \times 10^6$ cells/cm$^2$; $1.5 \times 10^6$ cells/cm$^2$ and $2.95 \times 10^6$ cells/cm$^2$; $1.3 \times 10^5$ cells/cm$^2$ and $2.5 \times 10^6$ cells/cm$^2$; or $1.3 \times 10^5$ cells/cm$^2$ and $2 \times 10^6$ cells/cm$^2$.

In a further embodiment, the contractile cells comprise a combination of immature contractile cells and mature contractile cells. In one such embodiment, the immature contractile cells and mature contractile cells are present on the construct surface in a ratio of between about 1:2 and about 2:1. In other embodiments, the ratio is between about 1:1 and about 2:1; or about 1:1 and about 1:2.

In one embodiment, the contractile cells comprise immature cardiomyocytes. In another embodiment, the contractile cells comprise mature cardiomyocytes. In one embodiment, the immature cardiomyocytes and/or the mature cardiomyocytes are seeded on the surface of the construct at a density of between $1.3 \times 10^5$ cells/cm$^2$ and $2.7 \times 10^6$ cells/cm$^2$ and the contractile cells are seeded on the surface of the 3DFCS in a ratio of between about 1:7 and about 3:1 with fibroblasts on the 3DFCS. In another embodiment, the immature cardiomyocytes and/or the mature cardiomyocytes are seeded on the surface of the construct at a total density of between $2.9 \times 10^5$ cells/cm$^2$ and $2.3 \times 10^6$ cells/cm$^2$. In various embodiments, the construct comprises a dose range of cardiomyocytes at $2.9 \times 10^5$ cells/cm$^2$, $1.2 \times 10^6$ cells/cm$^2$ or $2.3 \times 10^6$ cells/cm$^2$ for therapeutic use. Cardiomyocyte populations may be 100% mature cardiomyocyte or 100% immature cardiamyocytes, 50% mature cardiomyocytes and 50% immature cardiomyocytes, or any suitable variation thereof.

In another embodiment, the contractile cells comprise smooth muscle cells. In one such embodiment, the smooth muscle cells are seeded on the surface of the construct at a density of between $1.3 \times 10^5$ cells/cm$^2$ and $2.95 \times 10^6$ cells/cm$^2$ and the contractile cells are seeded on the surface of the 3DFCS in a ratio of between about 1:15 and about 3.5:1 with fibroblasts on the 3DFCS. In various embodiments, the smooth muscle cells are seeded on the surface of the 3DFCS in a ratio of between about 1:15 and 3.5:1; 1:15 and 1.7:1; 1:6 and 3.5:1; 1.6 and 1.5:1; or 1:1.7 and 1.5:1 with fibroblasts on the 3DFCS.

In various further embodiments, the smooth muscle cells are seeded on the surface of the construct at a density of between $1.3 \times 10^5$ cells/cm$^2$ and $2.94 \times 10^6$ cells/cm$^2$; $1.2 \times 10^6$ cells/cm$^2$ and $2.94 \times 10^6$ cells/cm$^2$; $1.3 \times 10^5$ cells/cm$^2$ and $1.2 \times 10^6$ cells/cm$^2$; or $1.0 \times 10^6$ cells/cm$^2$ and $1.2 \times 10^6$ cells/cm$^2$. In another embodiment, the smooth muscle cells are seeded on the surface of the construct at a density of between $1.0 \times 10^6$ cells/cm$^2$ and $1.2 \times 10^6$ cells/cm$^2$ and the smooth muscle cells are present on the surface of the 3DFCS in a ratio of between about 1:1.7 and about 1.5:1 with fibroblasts on the 3DFCS.

In a further embodiment, the contractile cells comprise skeletal muscle cells. In one such embodiment, the skeletal muscle cells are seeded on the surface of the construct at a density of between $1.3 \times 10^5$ cells/cm$^2$ and $2.95 \times 10^6$ cells/cm$^2$ and the skeletal muscle cells are seeded on the surface of the 3DFCS in a ratio of between about 1:15 and about 3.5:1 with fibroblasts on the 3DFCS. In various embodiments, the skeletal muscle cells are seeded on the surface of the 3DFCS in a ratio of between about 1:15 and 3.5:1; 1:15 and 1.7:1; 1:6 and 3.5:1; 1.6 and 1.5:1; or 1:1.7 and 1.5:1 with fibroblasts on the 3DFCS. In various further embodiments, the skeletal muscle cells are seeded on the surface of the construct at a density of between $1.3 \times 10^5$ cells/cm$^2$ and $2.94 \times 10^6$ cells/cm$^2$; $1.2 \times 10^6$ cells/cm$^2$ and $2.94 \times 10^6$ cells/cm$^2$; $1.3 \times 10^5$ cells/cm$^2$ and $1.2 \times 10^6$ cells/cm$^2$ or $1.0 \times 10^6$ cells/cm$^2$ and $1.2 \times 10^6$ cells/cm$^2$. In another embodiment, the skeletal muscle cells are seeded on the surface of the construct at a density of between $1.0 \times 10^5$ cells/cm$^2$ and $1.2.0 \times 10^6$ cells/cm$^2$ and the skeletal muscle cells are present on the surface of the 3DFCS in a ratio of between about 1:1.7 and about 1.5:1 with fibroblasts on the 3DFCS.

Suitable culture conditions can be determined by one of skill in the art, so long as the immature cardiomyocytes are cultured on the 3DFC. Any useful media may be used, including but not limited to DMEM-LG supplemented with fetal bovine serum (5-15%; preferably 10%) and other appropriate factors (including but not limited to sodium bicarbonate and antibiotics.

Contacting a cultured 3DFC with contractile cells to be seeded onto the 3DFC can be done under any suitable conditions to facilitate application of the force that causes the cells to contact the 3DFC. In one embodiment, the 3DFC is placed in media and cells are introduced in suspension, such that the volume of cell suspension is approximately double the volume of media in which the 3DFC is placed. In one alternative embodiment that can be combined with any other embodiments herein, the contacting occurs at approximately 37° C. Cell densities and ratios with fibroblasts on the 3DFC are as described herein In one embodiment, each 3DFC to be seeded is placed in a well so as to cover the base of the well and lay flat. Subjecting the cells within the suspension to a force that causes said cells to contact the 3DFC may comprise the use of any suitable force, including but not limited to a centrifugal force and an electrical force generated by an electric field, or combinations of such forces. In an alternative embodiment, a centrifugal force is used. The centrifugal force to be applied depends on a variety of factors, such as the cell type to be seeded onto the 3DFC. In one alternative embodiment that can be combined with any other embodiments herein, the construct is centrifuged at between 1200 rpms and 1600 rpms for between 2 and 10 minutes. In an alternative embodiment, all 3DFC constructs to be seeded are placed in a horizontal arrangement in wells (as opposed to vertical), so that each well is spun at the same radius.

In one embodiment, the culture medium is xenobiotic free. For example, the construct can be maintained at 37° C. and 5% $CO_2$. Culture media can be changed every 10 to 48 hrs with 24 hrs being preferable. Seeding and culture can occur in any tissue culture tested "open top" culture dishes such as 35 $mm^2$, 65 $mm^2$, 100 $mm^2$ or well plates, such as 96, 24, or 6 formats. Plates/dishes may be low adhesion or high adhesion. Contractile cells can be seeded and co-cultured on the 3DFC variance occur between cryopreserved, freshly isolated (from tissue) or from tissue culture preparations. Cryopreserved cells, freshly isolate cells from tissue, or live tissue culture cells can be directly seeded on the 3DFC by any suitable technique. Patches can be cultured for any suitable period of time as most appropriate for an intended use of the constructs. In one embodiment, the constructs will be used for transplantation and the culturing is carried out for 14-240 hours; in various further embodiments, the culturing is carried out between 14-120 hours; 14-36 hours, 14-48 hours, 14-22 hours, 24-240 hours, 24-120 hours, 24-72 hours, 24-48 hours, 48-240 hours, 48-120 hours, 48-72, 14-22 hours, 18-22 hours, less than 48 hours, less than 24 hours, less than 20 hours, less than 16 hours, or less than 14 hours prior to implantation.

In a further embodiment, the method further comprises transplanting the contractile construct into a subject in need thereof. In one embodiment, the constructs are not displaying cellular level or patch level contractions at the time of implantation. In this embodiment, implantation is carried out after adhesion of the cells on the construct has occurred but prior to the onset of contraction either cellular or patch level contractions so that the heart drives cellular alignment and integration to limit arrhythmias. In another embodiment, the constructs are implanted after cellular level and/or construct-level contractions are present.

The seeded patches typically begin cellular level contractions across the surface of the patch within 48 hrs, these contractions develop into full "patch" contractions where the underlying 3DFC can be seen visually contracting (per the video) after about 72 hrs. However, certain cell sources (such as cryopreserved cells) may require additional culture time before cell level contractions are detectable. Constructs can be cultured approximately 10 days as the vicryl mesh begins to break down through hydrolysis.

Once implanted, the methods of the invention can be carried out similarly to those disclosed herein. For example, when the immature contractile cells are immature cardiomyocytes and the mature contractile cells are mature cardiomyocytes, and the transplanting comprises contacting the heart of a subject suffering from such a disorder with an amount effective of the contractile construct to treat the disorder. In this embodiment, the disorder may include, but is not limited to ischemia-induced heart failure, chronic heart failure (CHF), ischemia without heart failure, cardiomyopathy, dilated cardiomyopathy (DCM), cardiac arrest, congestive heart failure, stable angina, unstable angina, myocardial infarction, coronary artery disease, valvular heart disease, ischemic heart disease, reduced ejection fraction, reduced myocardial perfusion, maladaptive cardiac remodeling, maladaptive left ventricle remodeling, reduced left ventricle function, left heart failure, right heart failure, backward heart failure, forward heart failure, systolic dysfunction, diastolic dysfunction, increased or decreased systemic vascular resistance, low-output heart failure, high-output heart failure, dyspnea on exertion, dyspnea at rest, orthopnea, tachypnea, paroxysmal nocturnal dyspnea, dizziness, confusion, cool extremities at rest, exercise intolerance, easy fatigueability, peripheral edema, nocturia, ascites, hepatomegaly, pulmonary edema, cyanosis, laterally displaced apex heat, gallop rhythm, heart murmurs, parasternal heave, and pleural effusion. All other embodiments of the methods of treatment as disclosed above can be used in this aspect of the invention.

In another embodiment, the method further comprises contacting the contractile construct with a compound of interest and determining an effect of the compound on one or more characteristics of the construct. This drug screening embodiment is described above, and embodiments disclosed therein can be used with this embodiment. For example, the method may comprise culturing the construct under conditions to promote contraction of the construct prior to contacting the construct with the compound of interest. In another embodiment, the effect of the compound on one or more of contraction displacement, contraction rate, contraction synchronicity, and contraction velocity are determined.

EXAMPLES

Patch Manufacturing

Seeding Methods—In brief centrifugal force is applied to the cells in suspension. The cell are driven/forced onto the surface of a 3 dimensional fibroblasts construct (3DFC), and we achieve a random yet uniform distribution of cells. The base construct (the 3DFC) provides support and the proper requirements for cell engraftment and alignment, and to generate a contractile force. The end "product" is a degradable mesh embedded with fibroblasts and over seeded with a contractile cell population, in this preparation, iPSC derived ("immature") cardiomyocytes.

Seeding Densities—The seeding density for inducible human pluripotent stem cells (hiPSC) seeding ranges from $0.3 \times 10^6$ cell/cm$^2$ to $2.4 \times 10^6$ cells/cm$^2$ with $1.2 \times 10^6$ cells/cm$^2$ being ideal.

Cell-Cell Ratios—the starting material for the cardiac patch is a 3DFC that includes a synthetic vicyrl mesh embedded with human dermal fibroblasts. The fibroblasts are angiogenic and thus provide nutrient support after implantation on the heart for the over seeded iPSC-derived cardiomyocytes population. Our data show that cell ratios (iPSC derived cardiomyocytes to dermal fibroblasts) range from 3:20 to 1.2:1 with 1.2:2 being ideal.

We have developed methods of electrically mapping the heart to study electrical stability and integration of the implanted patch. Electrical activation mapping was performed on the rat neonatal cardiomyocytes (NCM)-3DFC in tissue culture 5 days after co-culturing (10% FBS in DMEM, maintained at 37° C. and 5% $CO_2$. Culture media is changed every 24 hrs) using a custom designed multi-electrode array (MEA) with 18 recording sites spaced 500 µm apart (FIG. 1A). Recordings were performed from 10 electrodes; each recording site was numbered sequentially as channel 1-10 (FIG. 1B). The electrical activation of the patch showed consistent beat-to-beat activation as shown in 7 sec interval displaying the peak transverse conduction voltage for each individual channel (FIG. 1C). The amplitude is shown with all channels superimposed in a beat-to-beat sequence (FIG. 1D) and during a single activation (FIG. 1E). The amplitude was recorded as 0.03 to 0.42 and −0.13 to −0.75 mV (FIGS. 1D & E). These results demonstrate that the NCM-3DFC is electrically stable (FIG. 1), making it unlikely to elicit an arrhythmia when implanted.

We have pursued evaluation of human iPSCs seeded on the fibroblasts patch, and it shows trending improvement in regards to R wave amplitude. We have performed a complete functional study with human induced pluripotent stem cell derived cardiomyocytes (hiPSC-CMs) implanted 18±4 hrs after patch creation. Echocardiography was performed with views in the parasternal short axis and long axis, to evaluate the anterior, lateral, antero-lateral, inferior and posterior walls with a dedicated rodent echocardiography system (Vevo2100) at 3 and 6 weeks post-intervention to define LV systolic and diastolic function i.e., mitral valve inflow patterns, M-Mode for LV functional analysis, and Tissue Doppler for quantification of myocardial tissue movement in diastole (anterior LV wall) were used to assess function. Data is shown in Table 1.

The data show the hiPSC-CM-3DFC improve LV function three weeks after implantation by increasing EF 13%, tissue Doppler parameters E' 23%, E'/a' 33% ($p<0.05$) while decreasing ($p<0.05$) EDP 47%, Tau 18% and E/e' 23%. Passive pressure volume relations show a left shift towards the pressure axis toward normal with hiPSC-CM-3DFC patch treatment. These data support improvements in passive filling and chamber stiffness of the LV with respect to a decrease in operating LVEDP and shown in the hemodynamics. No functional improvements were observed with 3DFC implantation alone.

Figure 2:
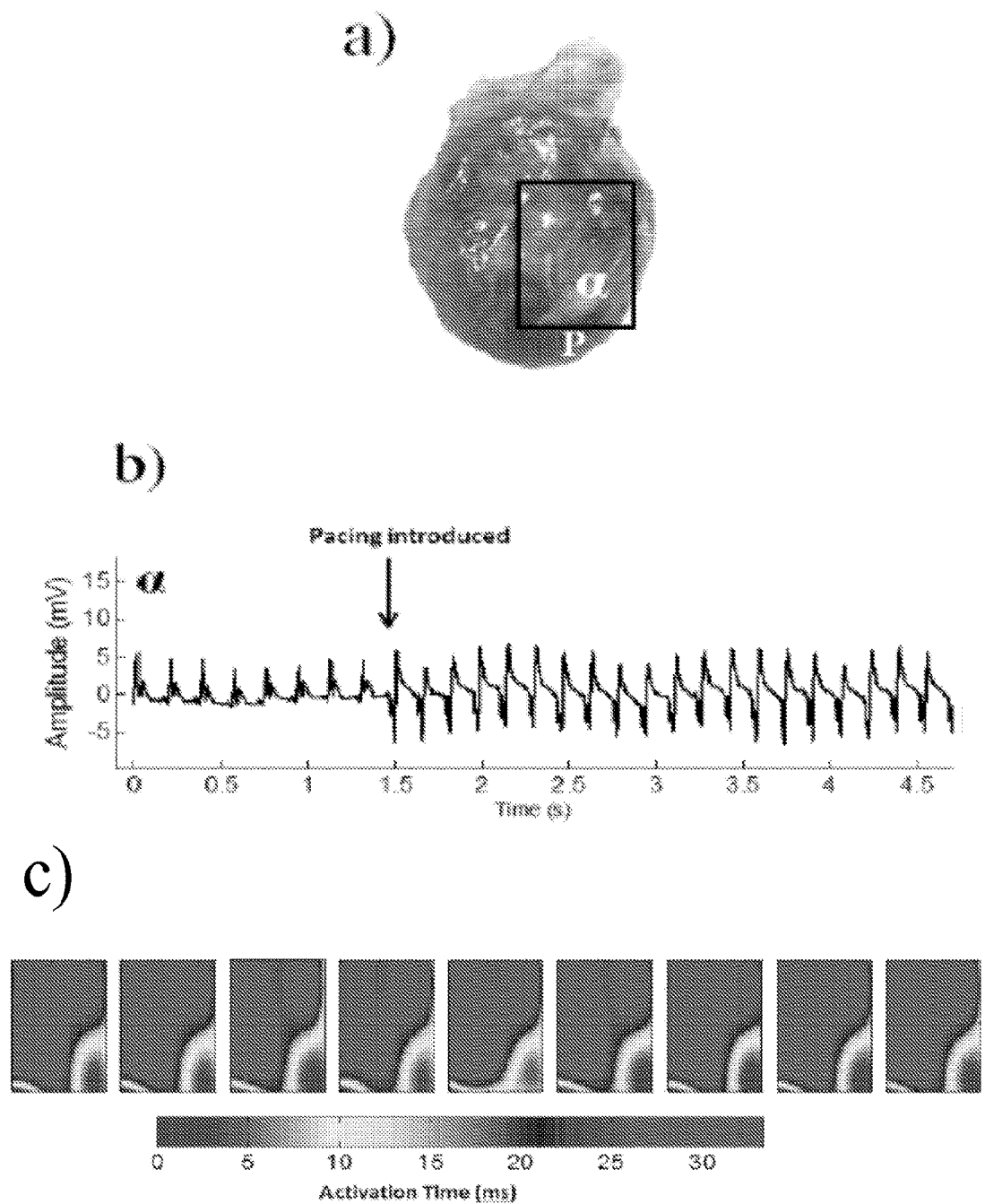
FIG. 2. a) Paced activation map in chronic heart failure (CHF) rat with seeded patch for region of interest indicated by black box, b) Electrogram taken from epicardial surface during introduction of pacing electrodes at location 'P' shows successful capture. c) Activation times compiled over 72 contractions at 32 locations provides data for 9 distinct activation maps. Multiple maps created indicate consistency in measurement.
Figure 3:
FIG. 3. Inducible pluripotent stem cell derived cardiomyocytes (stained red) were seeded and co-cultured on the fibroblast construct. The vicryl fibers can be seen as the woven, net like mesh. Deep to the red fluorescence are the embedded fibroblasts. The cells were seeded topically and do not penetrate into the patch or embedded fibroblasts. The patches began spontaneously and synchronously contracting shortly after seeding. Cells were seeded in a random fashion using centrifugal force.

Electrical integration was performed and assessed by peak voltage amplitude and conduction velocity (FIG. 3). Human iPSCs seeded on the 3DFC showed trending improvement with respect to voltage (FIG. 2). To evaluate voltage, a) we generated a paced activation map in a rat model of chronic heart failure (CHF) with seeded patch for region of interest indicated by black box (FIG. 2a). b) An electrogram taken from the epicardial surface during introduction of pacing electrodes at location 'P' shows successful capture (FIG. 2b). Activation times compiled over 72 contractions at 32 locations provides data for 9 distinct activation maps are shown (FIG. 2c). Multiple maps created indicated consistency in measurement of activation time (ms) and amplitude (mV). These results regarding improvement in R wave amplitude and voltage are significant because they show the cells seeded on the patch, while excitable electromechanically couple the heart tissue.

Patches seeded with human iPSCs-derived cardiomyocytes beat spontaneously in a synchronized fashion, generated force, can be electrically paced, and implanted with ease.

Human inducible pluripotent stem cell derived cardiomyocytes (stained red) were seeded and co-cultured on the fibroblast construct (FIG. 3). The vicyrl fibers can be seen as the woven, net like mesh. Deep to the red fluorescence are the embedded fibroblasts. The cells were seeded topically and did not penetrate into the patch or embedded fibroblasts. The patches began spontaneously and synchronously contracting shortly after seeding. Cells were seeded in a random fashion using centrifugal force.

Contractions of the patches are described in two ways: 1) cellular contraction and 2) patch level contraction. In cellular level contractions, the seeded contractile cells are contractile in a synchronized and spontaneous nature but are not capable of moving the 3DFC, a microscope is required for visualization. Patch level contractions develop after the

TABLE 1

|  | HR bpm | EF % | E' mm/sec | E/E' | LV Sys BP mmHg | LV EDP mmHg | LV dP/dt+ mmHg/sec | Tau msec |
|---|---|---|---|---|---|---|---|---|
| Sham | 326 ± 25 | 78 ± 1 | 37.1 ± 12.5 | 12.9 | 135 ± 4 | 7 ± 2 | 7834 ± 400 | 16.6 ± 3.6 |
| CHF | 287 ± 11 | 54 ± 12 | 22.0 ± 1.2** | 30.0 ± 3.1** | 137 ± 4 | 19 ± 3** | 6587 ± 467* | 30.9 ± 3.2** |
| Patch | 286 ± 10 | 64 ± 5 | 33.3 ± 6.5* | 22.4 ± 4.6* | 131 ± 3 | 11 ± 2* | 6274 ± 779 | 21.8 ± 1.6* |

Legend:
HR, heart rate.
LV Sys BP, Systolic Blood Pressure.
LV EDP, Left Ventricular End Diastolic Pressure.
E', Early diastolic velocity of the anterior wall of LV.
E, Peak velocity of early mitral flow.
LV dP/dt, first derivative of LV pressure.
Values are mean ± SEM.
*$P < 0.05$ vs CHF;
**$P < 0.05$ vs Sham. (Ns = 1-12).

cells have organized and aligned and result in movement or contraction of the entire patch on a gross level, not requiring any microscopy for visualization. The seeded patches will begin cellular level contractions across the surface of the patch within 48 hrs, these contractions develop into full "patch" contractions where the underlying 3DFC can be seen visually contracting after about 72 hrs. Patches can be cultured approximately 10 days as the vicryl mesh begins to break down through hydrolysis. After the 10 day culture window the patches loose there structural integrity.

Figure 4:
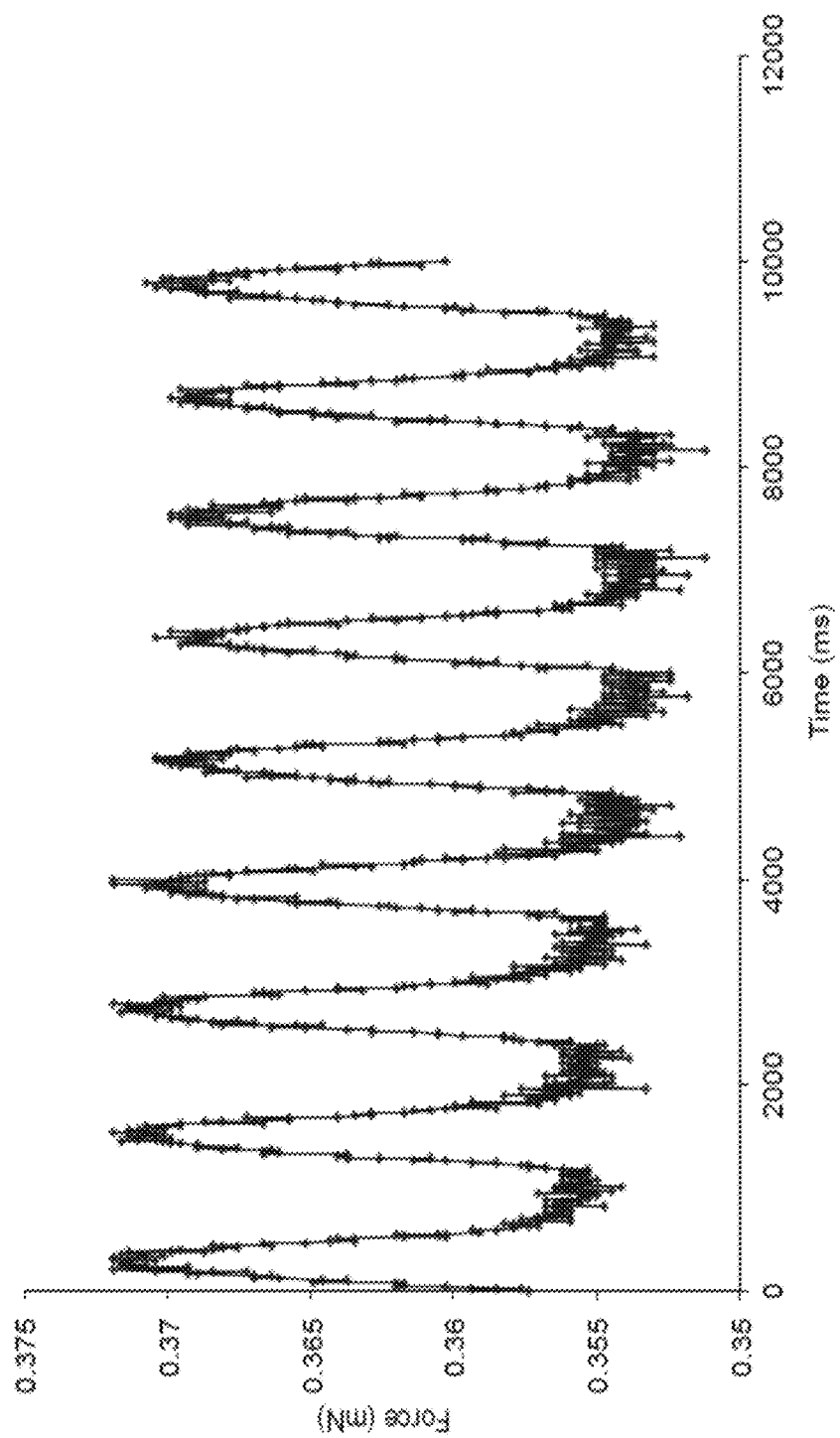
FIG. 4. Inducible pluripotent stem cell derived cardiomyocytes when seeded on the fibroblast patch generated a force response. Data are from fibroblast patches seeded with $2 \times 10^6$ cells each ($1.2 \times 10^6$ cells/cm2) 5 days after culture. This demonstrates that the iPSC derived cardiomyocytes align and contracted in a unison fashion and may potentially aid in in the resulting functional improvements.

As shown in FIG. 4, human inducible pluripotent stem cell derived cardiomyocytes when seeded on the fibroblast patch generated a force response. Data are from fibroblast patches seeded with $2 \times 10^6$ cells each ($1.2 \times 10^6$ cells/cm$^2$) 5 days after culture. Force measurements were performed using a small intact fiber test apparatus (Aurora Scientific Inc—models 801C) with thermo control and perfusion capabilities. Patches were generated and cultured as described between one and six days. Patches where then trimmed into sections approximately 2 mm×17 mm and attached to the force transducer. During force experiments, both the transducer well and perfusate were maintained at 37° C. Resting tension was achieved prior to acquiring force generation. Force generation demonstrates that the iPSC derived cardiomyocytes align and contracted in a unison fashion and may potentially aid in in the resulting functional improvements.

Figure 5:
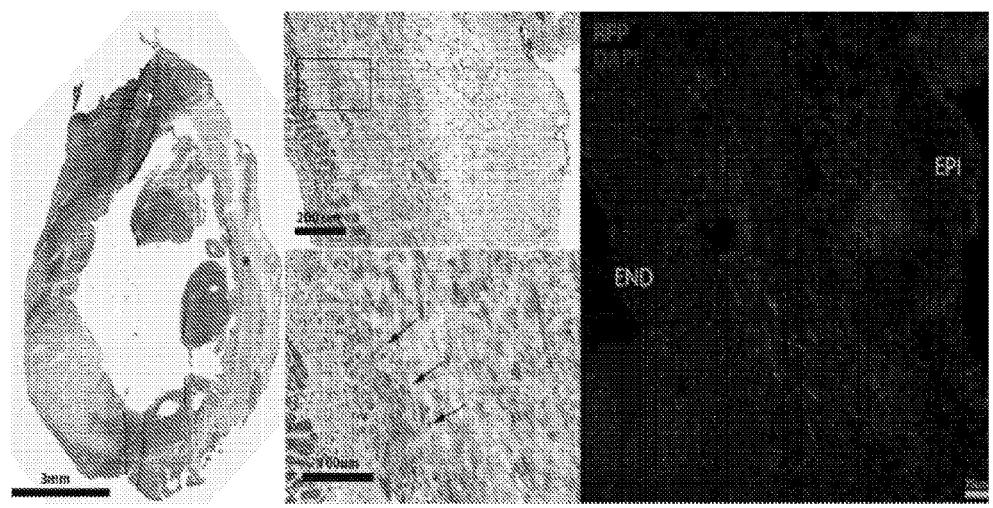
FIG. 5. Trichrome stain shows cross-section three weeks after patch implantation. Corresponding asterisk and box denotes area of higher magnifications. Arrows denote band of myocytes, which express RFP as represented by the fluorescent image on the right. Epicaridium (EPI) and endocardium (END) are labeled for orientation. Positive Red Fluorescent positive cells suggest human iPSC-dCM survival as denoted by the presence of RFP expression (red). Tissue and construct nuclei are DAPI (blue) labeled. As expected, the human iPSC-dCMs remain localized 3 weeks after implantation.

Pathophysiologically, ischemia induced CHF is denoted by dilatation of the LV as a compensatory means to preserve cardiac output in addition to thinning of the anterior and anterior-lateral. These regions become relatively void of viable cardiomyocytes due to the ischemic nature of the tissue, which results in decreased cardiac contractility and performance. Therapeutics strategies such as cell-base tissue engineering associated with CHF may include cell replacement via exogenous, endogenous, or a combination thereof to repopulate the infarct regions with viable cardiomyocytes. As shown in FIG. 5, hiPSC-CM-3DFC helps facilitate replacement of cardiomyocytes into the infarcted region.

Figure 6:
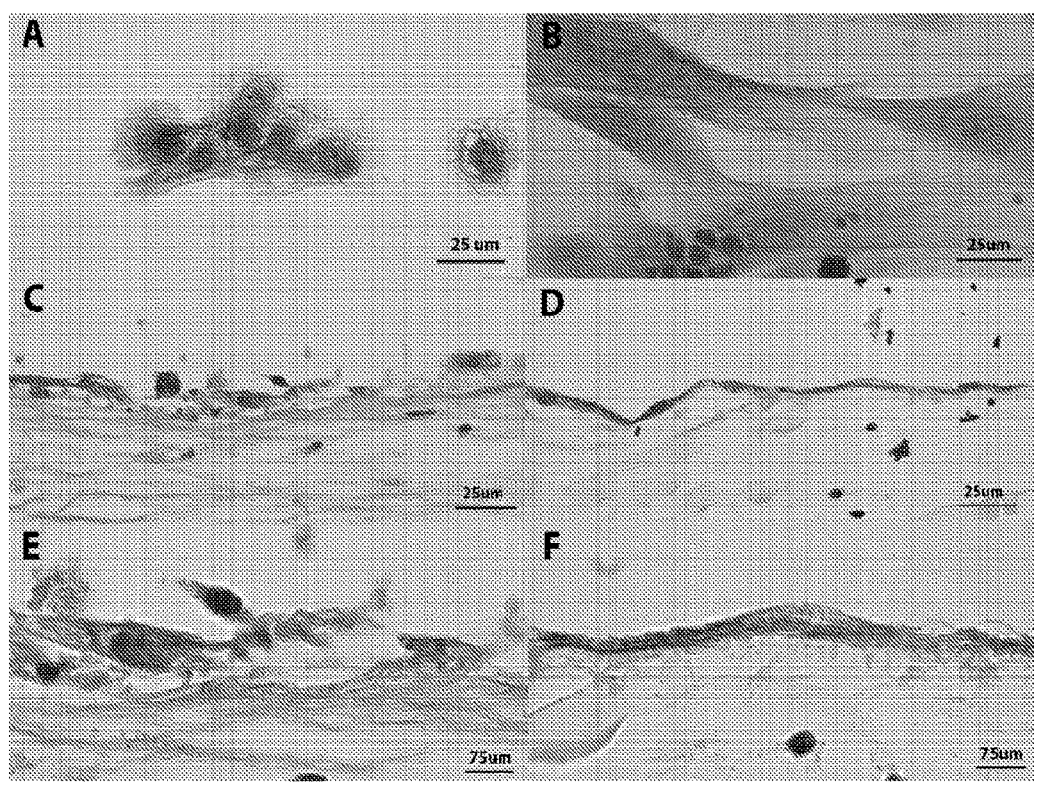
FIG. 6. Trichrome stain of human induced pluripotent stem cell derived cardiomyocytes (hiPSC-CMs) at two (A) versus six (B) days in standard tissue culture. At both two and six days in culture, all cells stain positive (red/purple) for muscle. After six days in culture the hiPSC-CMs were enlarged. When seeded on the fibroblast patch, at two days (C&E) the hiPSC-CMs remain small in size, by six days (D&F) the hiPSC-CMs have developed into an intact layer in which striations are clearly present suggesting that the fibroblast patch provides structural support permitting maturation of the hiPSC-CMs in vitro.

Maturation of cardiomyocytes for therapeutic or various in vitro assays may be of importance. Therapeutically, maturation of the cardiomyocyte may help facilitate force generation and thus greater recover of LV function while providing a more tissue like and therefore physiologically representative in vitro assay. Maturation of hiPSCs was evaluated after culture on a fibroblast constructs (3DFC) (FIG. 6). Trichrome stain of human induced pluripotent stem cell derived cardiomyocytes (hiPSC-CMs) at two (A) versus six (B) days in standard tissue culture. At both two and six days in culture, all cells stain positive for muscle. After six days in culture the hiPSC-CMs were enlarged. When seeded on the fibroblast patch, at two days (C&E) the hiPSC-CMs remain small in size, by six days (D&F) the hiPSC-CMs have developed into an intact layer in which striations are clearly present suggesting that the fibroblast patch provides structural support permitting maturation of the hiPSC-CMs in vitro.

Figure 7:
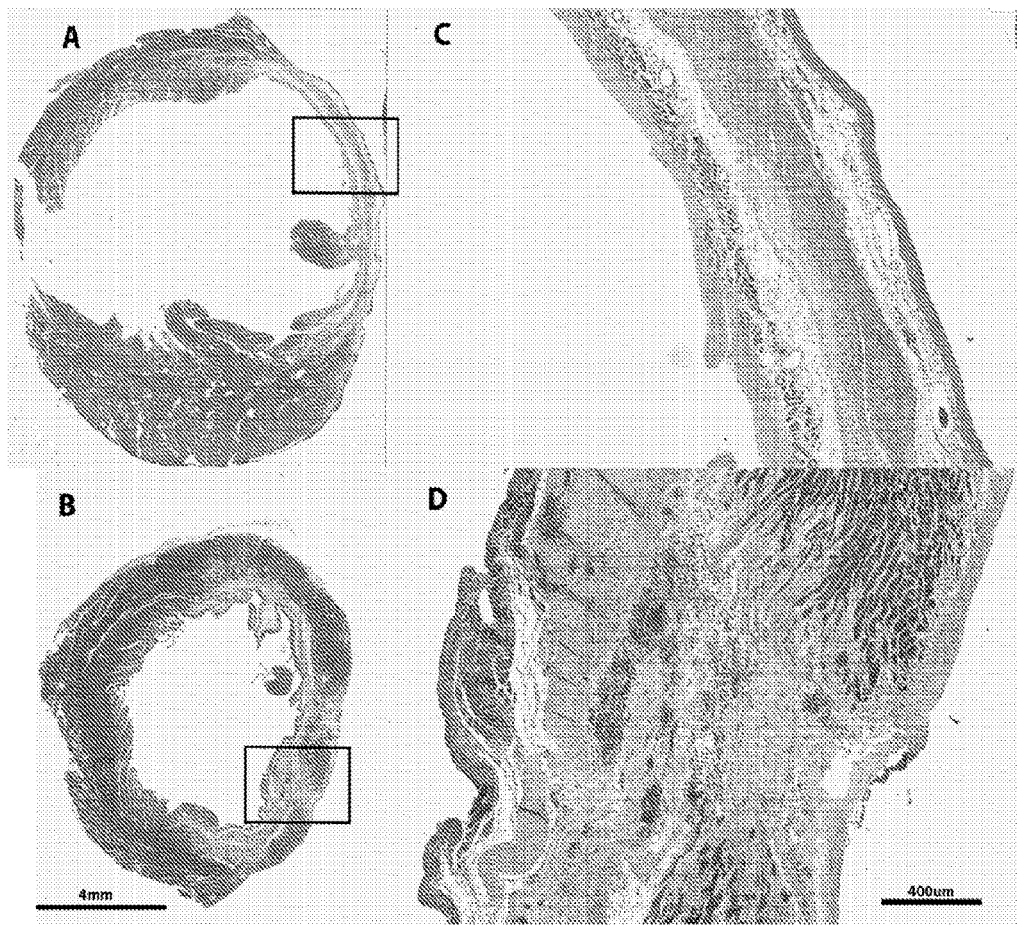
FIG. 7. Trichrome-stained left ventricular cross sections (A&B) of 6 wk chronic heart failure (CHF) control receiving an infarct but no treatment, (C&D) CHF+human induced pluripotent stem cell derived cardiomyocytes patch (hiPSC-CM) 6 weeks after coronary artery ligation (3 weeks after implantation). Hearts were excised, right ventricles removed and cut into 5 μm transverse sections along the midpoint of the ventricle. Healthy myocardium is represented as red-purple, collagen/scar as blue, and red blood cells as small red dots. Box insets represent area of higher magnification. Implantation of the hiPSC-CM patch results in increased LV wall thickness (D) and preservation and/or generation of myocardium (D).

Furthermore, we show that implantation of the hiPSC-CM patch results in increased anterior wall thickness and increased viable myocardium either through endogenous means, cell transplantation or a combination of the two (FIG. 7).

We assessed expression of mRNA via Real-Time PCR in CHF treated with a human iPSC-derived cardiomyocyte patch. The data shows that the hiPSC-derive cardiomyocytes cardiac patches result in up regulation of angiopoietin 1 (ANG-1), Connexin 43 (Cx43), and vascular endothelial growth factor (VEGF) mRNA expression levels in LV heart tissue (Table 2). While the 3DFC alone does not significantly increase VEGF and ANG-1 expression, delivery of hiPSC-CM-3DFC results in a dose dependent increase in expression. The VEGF and ANG-1 expression may be a mechanistic contributor towards microvascular formation, which may provide endogenous nutrient support of tissue regeneration. Furthermore, Cx43 expression may be confirmatory of cardiomyocyte repopulation of the LV and a restoration of function.

TABLE 2

Expression of mRNA via Real Time PCR in Heart Failure Treated with iPSCs Patch

| Treatment Groups | VEGF | ANG-1 | Cx43 |
|---|---|---|---|
| Sham | 1.0 ± 0.2 | 0.9 ± 0 | 1.2 ± 0.4 |
| CHF | 0.6 ± 0.2 | 0.5 ± 0.3 | 2.0 ± 0.2 |
| 3DFC | 0.8 ± 0.3 | 0.7 ± 0.4 | 3.0 ± 0.2* |
| hiPSC-CM-3DFC 0.5M | 2.8 ± 0.2* | 2.1 ± 0.2* | 3.6 ± 0.2* |
| hiPSC-CM-3DFC 2M | 3.6 ± 0.2* | 2.0 ± 0.1* | 4.0 ± 0.4* |
| hiPSC-CM-3DFC 4M | 4.9 ± 0.2* | 6.6 ± 0.8* | 2.3 ± 0.7 |

Data are relative expression compared of VEGF, ANG-1 or Cx43 expression in heart failure rats. Expression is compared to healthy rats, and represent mRNA expression 6 weeks post infarction, 3 weeks post patch implantation. Data represent mean ± SE and compared to CHF group for evaluation of significant change in expression with patch.
*p < 0.05. Sham = 4, CHF = 6, 3DFC = 8, hiPSC-CM-3DFC 0.5M = 18, hiPSC-CM-3DFC 2M = 9 hiPSC-CM-3DFC 4M = 6.

REFERENCES

1. Thai, H. M., Juneman, E., Lancaster, J., Hagerty, T., Do, R., Castellano, L., Kellar, R., Williams, S., Sethi, G., Schmelz, M., Gaballa, M., & Goldman, S. (2009). Implantation of a three-dimensional fibroblast matrix improves left ventricular function and blood flow after acute myocardial infarction. *Cell Transplant.*, 18(3), 283-295. PMC2739416:PM19558777. doi:10.3727/096368909788535004
2. Lancaster, J., Juneman, E., Hagerty, T., Do, R., Hicks, M., Meltzer, K., Standley, P., Gaballa, M., Kellar, R., Goldman, S., & Thai, H. (2010). Viable fibroblast matrix patch induces angiogenesis and increases myocardial blood flow in heart failure after myocardial infarction. *Tissue Eng. Part A.*, 16(10), 3065-3073. PM20486785. doi: 10.1089/ten.TEA.2009.0589
3. Lancaster, J. J., Arnce, S. A., Johnson, N. M., Juneman, E. B., Thai, H. M., Kellar, R. S., Vitorin, J. E., Burt, J. M., Bahl, J. J., & Goldman, S. (2010). In vivo evaluation of a biologically active cardiomyocyte seeded scaffold to treat chronic head failure. [abstract]. Paper presented at the *Heart Failure Society of America: 14th Annual Scientific Meeting*, San Diego, Calif., 16(8) S45. doi: 10.1016/j.cardfail.2010.06.155
4. Lancaster, J. J., Arnce, S. A., Johnson, N. M., Juneman, E. B., Thai, H. M., Kellar, R. S., Vitorin, J. E., Burt, J. M., Gaballa, M. A., Bahl, J. J., & Goldman, S. Tissue engineered scaffold seeded with cardiomyocytes improves cardiac function in rats with chronic ischemic heart failure disease. (Journal of Heart and Lung Transplantation).

We claim:
1. A method for treating a disorder characterized by a lack of functioning contractile cells, comprising
   contacting a patient with a contractile cell-based disorder with an amount effective to treat the disorder of a construct comprising contractile cells, or progenitors thereof, adhered to a surface of a three dimensional fibroblast containing scaffold (3DFCS), wherein the construct is capable of spontaneous synchronized contractions across the surface of the 3DFCS, wherein the contractile cells are seeded on the surface of the construct at a density of between $1.3 \times 10^5$ cells/cm$^2$ and less than $5 \times 10^5$ cells/cm$^2$, wherein the contractile cells are present on the surface of the 3DFCS in a ratio of between about 1:15 and about 6:1 with fibroblasts on the 3DFCS, wherein the contractile cells are immature cardiomyocytes, mature cardiomyocytes, or combinations thereof.

2. The method of claim 1, wherein the method comprises contacting the heart of a subject suffering from such a disorder with an amount effective of the construct to treat the disorder.

3. The method of claim 2, wherein the disorder is selected from the group consisting of ischemia-induced heart failure, chronic heart failure (CHF), ischemia without heart failure, cardiomyopathy, dilated cardiomyopathy (DCM), cardiac arrest, congestive heart failure, stable angina, unstable angina, myocardial infarction, coronary artery disease, valvular heart disease, ischemic heart disease, reduced ejection fraction, reduced myocardial perfusion, maladaptive cardiac remodeling, maladaptive left ventricle remodeling, reduced left ventricle function, left heart failure, right heart failure, backward heart failure, forward heart failure, systolic dysfunction, diastolic dysfunction, increased or decreased systemic vascular resistance, low-output heart failure, high-output heart failure, dyspnea on exertion, dyspnea at rest, orthopnea, tachypnea, paroxysmal nocturnal dyspnea, dizziness, confusion, cool extremities at rest, exercise intolerance, easy fatigue ability, peripheral edema, nocturia, ascites, hepatomegaly, pulmonary edema, cyanosis, laterally displaced apex beat, gallop rhythm, heart murmurs, parasternal heave, and pleural effusion.

4. The method of claim 2, where the disorder comprises CHF.

5. The method of claim 2, where the disorder comprises ischemia-induced heart failure.

6. The method of claim 2, wherein the construct is attached to the epicardium of the subject.

7. The method of claim 6, wherein the construct is non-contracting at the time of contacting with the epicardium.

8. The method of claim 6, wherein the construct is contracting at the time of contacting with the epicardium.

9. The method of claim 1, wherein the contacting comprises contacting the construct to the subject's left ventricle.

10. The method of claim 1, further comprising contacting the subject's heart with one or more of thymosin beta-4 (TB4), akt murine thymoma viral oncogene homolog (AKT1), stromal cell-derived factor-1 alpha (SDF-1), and hepatocyte growth factor (HGF).

11. The method of claim 1, wherein the treating comprises one or more of improving left ventricular function, decreasing left ventricular end diastolic pressure (EDP), improving myocardial perfusion, repopulating of the heart's wall with cardiomyocytes, reversing maladaptive left ventricle remodeling in CHF subjects, improvement in left ventricular passive filling, active filling, chamber compliance and parameters of heart failure including, but not limited to increasing E' (mm/s), decreasing E/E', increasing LV dP/dt (mmHg/sec) and decreasing Tau (msec).

12. The method claim 1, wherein the cardiomyocytes on the construct electrically integrate into the subject's native myocardium.

13. A method for treating a disorder characterized by a lack of functioning contractile cells, comprising contacting a patient with a contractile cell-based disorder with an amount effective to treat the disorder of a construct comprising contractile cells, or progenitors thereof, adhered to a surface of a three dimensional fibroblast containing scaffold (3DFCS), wherein the construct is capable of synchronized contractions across the surface of the 3DFCS, wherein the contractile cells are seeded on the surface of the construct at a density of between $1.0 \times 10^5$ cells/cm$^2$ and $2.95 \times 10^6$ cells/cm$^2$, wherein the contractile cells are present on the surface of the 3DFCS in a ratio of between about 1:15 and about 6:1 with fibroblasts on the 3DFCS, wherein the contractile cells are immature skeletal muscle cells, mature skeletal muscle cells, or combinations thereof.

14. The method of claim 13, wherein the disorder is selected from the group consisting of neuromuscular disease, degenerative disease, inflammatory disease, autoimmune muscle disease, sports injuries, war injuries, post-traumatic injuries, muscle wasting injuries, burn injuries, hernias, and chronic obstructive pulmonary disease.

15. A method for treating a disorder characterized by a lack of functioning contractile cells, comprising contacting a patient with a contractile cell-based disorder with an amount effective to treat the disorder of a construct comprising contractile cells, or progenitors thereof, adhered to a surface of a three dimensional fibroblast containing scaffold (3DFCS), wherein the construct is capable of synchronized contractions across the surface of the 3DFCS, wherein the contractile cells are seeded on the surface of the construct at a density of between $1.0 \times 10^5$ cells/cm$^2$ and $2.95 \times 10^6$ cells/cm$^2$, wherein the contractile cells are present on the surface of the 3DFCS in a ratio of between about 1:15 and about 6:1 with fibroblasts on the 3DFCS, wherein the contractile cells are immature smooth muscle cells, mature smooth muscle cells, or combinations thereof.

16. The method of claim 15, wherein the disorder is selected from the group consisting of peripheral artery disease, atherosclerosis, aneurysms, burn injuries, neuromuscular disease, degenerative disease, inflammatory disease, autoimmune muscle disease, sports injuries, war injuries, post-traumatic injuries, and muscle wasting injuries.

* * * * *